United States Patent
Ouchi et al.

(10) Patent No.: US 11,760,717 B2
(45) Date of Patent: Sep. 19, 2023

(54) RESIN COMPOSITION AND FLUIDITY IMPROVEMENT METHOD

(71) Applicant: Osaka Gas Chemicals Co., Ltd., Osaka (JP)

(72) Inventors: Yuki Ouchi, Osaka (JP); Shinichi Kamei, Osaka (JP); Tomoharu Tachikawa, Osaka (JP); Tomoya Hasegawa, Osaka (JP); Haruka Katakura, Osaka (JP)

(73) Assignee: OSAKA GAS CHEMICALS CO., LTD., Osaka (JP)

( * ) Notice: Subject to any disclaimer, the term of this patent is extended or adjusted under 35 U.S.C. 154(b) by 0 days.

(21) Appl. No.: 17/800,753

(22) PCT Filed: Dec. 21, 2020

(86) PCT No.: PCT/JP2020/047700
§ 371 (c)(1),
(2) Date: Aug. 18, 2022

(87) PCT Pub. No.: WO2021/171756
PCT Pub. Date: Sep. 2, 2021

(65) Prior Publication Data
US 2023/0102437 A1   Mar. 30, 2023

(30) Foreign Application Priority Data
Feb. 28, 2020 (JP) .................. 2020-034017

(51) Int. Cl.
| | | |
|---|---|---|
| *C07C 233/08* | (2006.01) | |
| *C08K 5/20* | (2006.01) | |
| *C08K 7/14* | (2006.01) | |
| *C08L 77/06* | (2006.01) | |

(52) U.S. Cl.
CPC .............. *C07C 233/08* (2013.01); *C08K 5/20* (2013.01); *C08K 7/14* (2013.01); *C08L 77/06* (2013.01); *C07C 2603/12* (2017.05)

(58) Field of Classification Search
CPC ............ C07C 2603/12; C07C 2603/18; C07C 233/08; C08K 5/20
See application file for complete search history.

(56) References Cited

U.S. PATENT DOCUMENTS 2,299,948 A   10/1942   Bruson

FOREIGN PATENT DOCUMENTS

| EP | 4 112 596 | 1/2023 |
|---|---|---|
| JP | 2009-139214 | 6/2009 |
| JP | 2015-218265 | 12/2015 |
| JP | 2017-210514 | 11/2017 |
| JP | 2019-1854 | 1/2019 |
| WO | 2014/168108 | 10/2014 |
| WO | 2016/139826 | 9/2016 |
| WO | 2017/026250 | 2/2017 |

OTHER PUBLICATIONS

International Search Report (ISR) dated Mar. 2, 2021 in International (PCT) Application No. PCT/JP2020/047700.
Sidney Baldwin, "The Synthesis of Spiro[cyclohexane-1,9'-fluorene] and Related Compounds", Journal of Organic Chemistry, vol. 26, pp. 3280-3287, 1961, cited in ISR.
Decision to Grant dated Mar. 29, 2022 in corresponding Japanese Patent Application No. 2022-503114, together with English translation thereof.
Notice of Reasons for Refusal dated Mar. 1, 2022 in corresponding Japanese Patent Application No. 2022-503114, together with English translation thereof.
International Preliminary Report on Patentability and Written Opinion of the International Searching Authority dated Aug. 30, 2022 in International (PCT) Application No. PCT/JP2021/047700.
Extended European Search Report dated Jun. 19, 2023 in corresponding European Patent Application No. 20921857.7.
Kretov, A.E. et al., "Preparation of 9,9-bis(β-cyanoethyl)fluorene and its derivatives from technical fluorene", Zhurnal Prikladnoi Khimii (Sankt-Peterburg, Russian Federation), 34, 1386-1389 (1961), with CAPLUS Database Abstract, AN 1961:124715.

*Primary Examiner* — Ana L. Woodward
(74) *Attorney, Agent, or Firm* — Wenderoth, Lind & Ponack, L.L.P.

(57) ABSTRACT

The resin composition of the present disclosure contains a fluorene derivative represented by the following formula (1) and a polyamide-series resin:

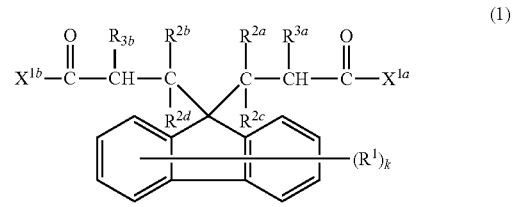

Wherein $R^1$ represents a substituent, k denotes an integer of 0 to 8, $R^{2a}$, $R^{2b}$, $R^{2c}$, and $R^{2d}$ each represent a hydrogen atom or a substituent, $R^{3a}$ and $R^{3b}$ each represent a hydrogen atom or a substituent, and $X^{1a}$ and $X^{1b}$ each represent a group defined in the following formula (X1):

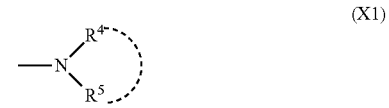

wherein $R^4$ and $R^5$ each represent a hydrogen atom or a hydrocarbon group; or $R^4$ and $R^5$ bend together to form a heterocyclic ring containing the nitrogen atom adjacent to $R^4$ and $R^5$.
The resin composition has an excellent fluidity.

9 Claims, 4 Drawing Sheets

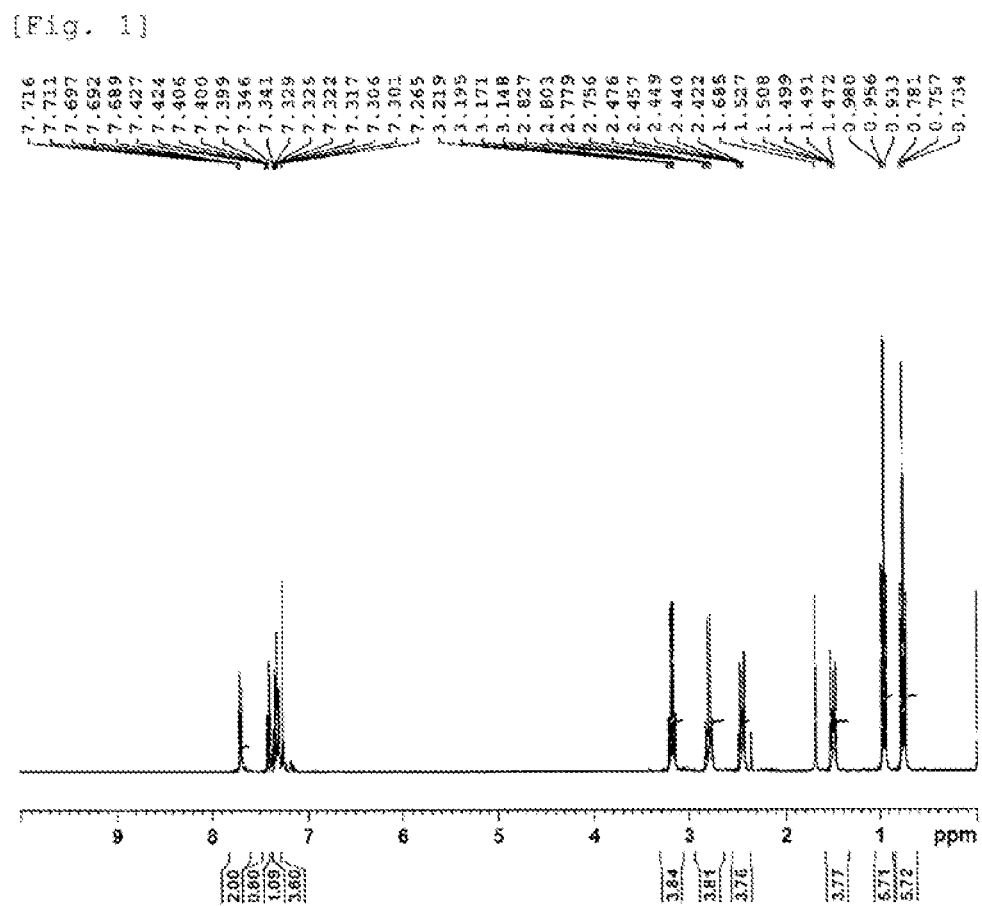

[Fig. 2]
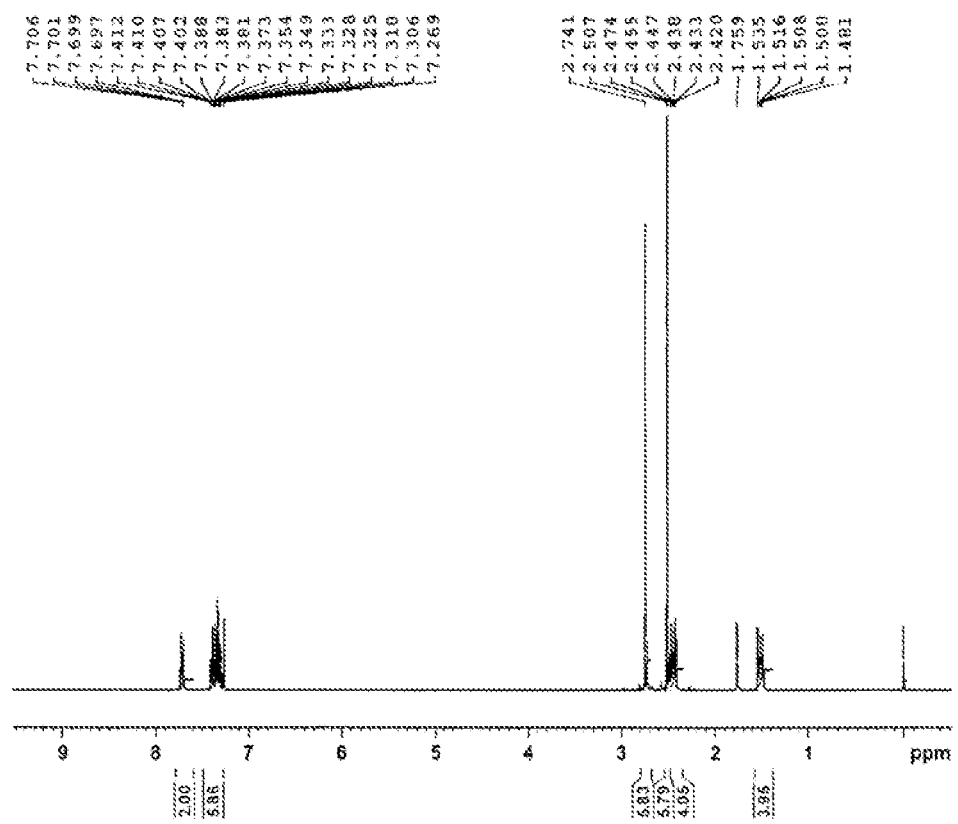

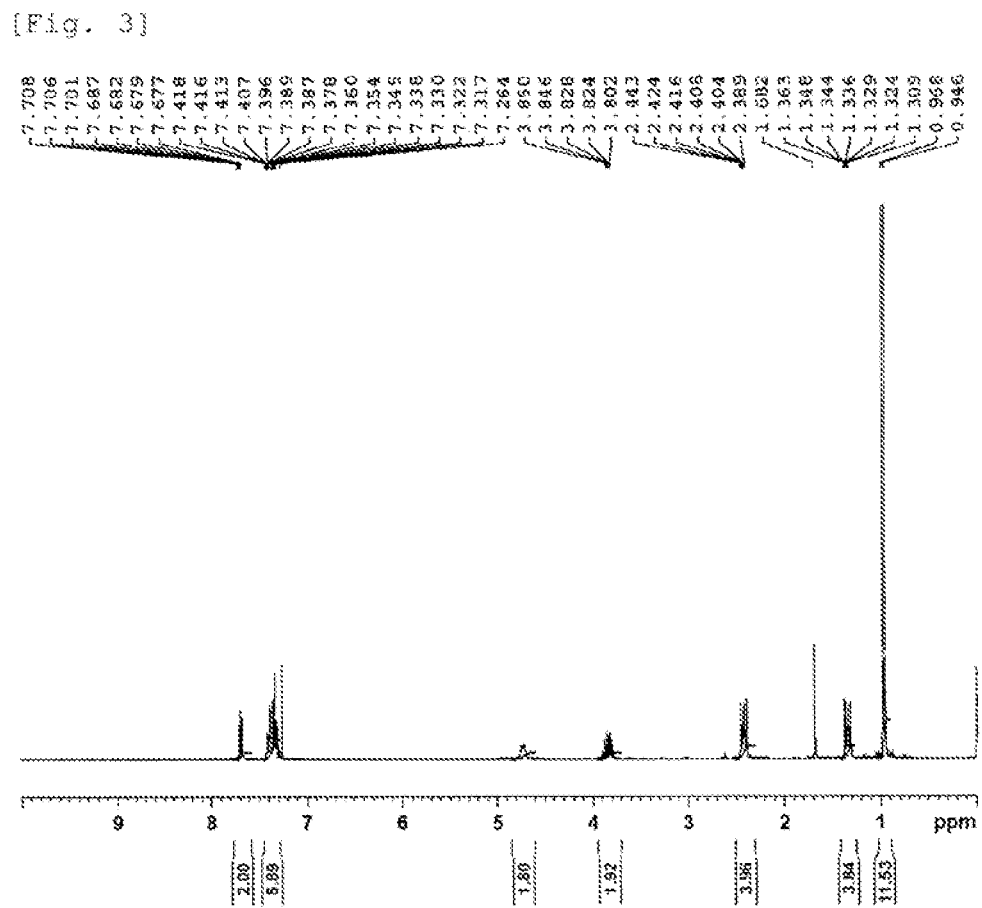

[Fig. 4]
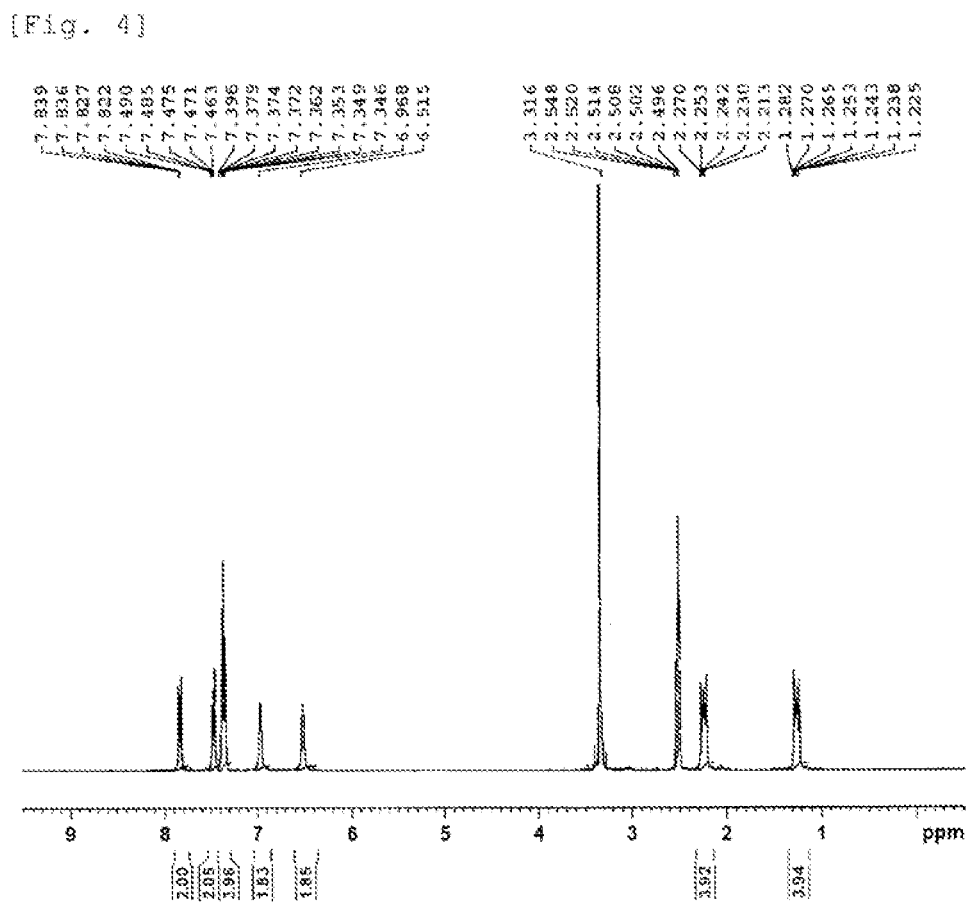

RESIN COMPOSITION AND FLUIDITY IMPROVEMENT METHOD

TECHNICAL FIELD

The present disclosure relates to a polyamide-series resin composition and a method for improving a fluidity thereof.

BACKGROUND ART

A fluorene derivative has been developed in various fields as a material for forming or producing an organic semiconductor, and art optical member, and other materials by utilizing excellent characteristics based on a specific chemical structure thereof, and is usually used as a monomer component for a resin. U.S. Pat. No. 2,299,948 (U.S. Pat. No. 2,299,943 A) (Patent Document 1) discloses that 9,9-di-(β-carbamoyl-ethyl)fluorene represented by the following formula is useful as an intermediate for preparing a synthetic resin.

[Chem. 1]

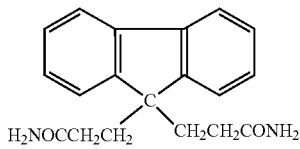

CITATION LIST

Patent Literature

Patent Document 1: U.S. Pat. No. 2,299,940 (U.S. Pat. No. 2,299,548 A)

SUMMARY OF INVENTION

Technical Problem

In Examples of Patent Document 1, the above-mentioned 9,9-di-(β-carbamoyl-ethyl)fluorene is prepared by reacting 9,9-di-(β-cyanoethyl)fluorene with sulfuric acid under predetermined conditions.

However, it has not been known the use of 9,9-di-(β-carbamoyl-ethyl)fluorene as an additive for improving properties, specifically a melt fluidity, of a polyamide-series resin, and Patent Document 1 also neither describe nor suggest, these matters.

It is therefore an object of the present disclosure to provide a polyamide-series resin composition having an excellent fluidity.

Solution to Problem

The inventors of the present invention made intensive studies to achieve the above object and finally found that the addition of a fluorene derivative with a specific chemical structure to a polyamide-series resin can greatly improve a fluidity of the polyamide-series resin. The present invention was accomplished based on the above findings.

That is, the resin composition of the present disclosure contains a compound represented by the following formula (1) (a fluorene derivative) and a polyamide-series resin.

[Chem. 2]

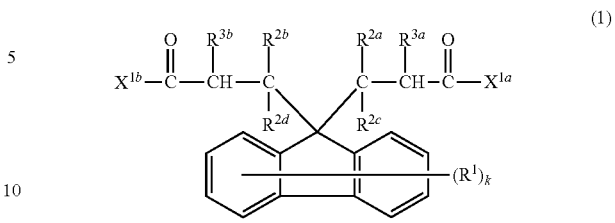

In the formula (1), $R^1$ represents a substituent, k denotes an integer of 0 to 8, $R^{2a}$, $R^{2b}$, $R^{2c}$, and $R^{2d}$ independently represent, a hydrogen atom or a substituent, $R^{3a}$ and $R^{3b}$ independently represent a hydrogen atom or a substituent, and $X^{1a}$ and $X^{1b}$ independently represent a group defined in the following formula (X1):

[Chem. 3]

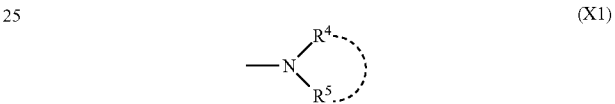

wherein $R^4$ and $R^5$ independently represent hydrogen atom or a hydrocarbon group; or $R^4$ and $R^5$ bond together to form a heterocyclic ring containing the nitrogen atom adjacent to $R^4$ and $R^5$.

In the formula (1), $R^{2a}$ and $R^{2b}$ each may represent a hydrogen atom, an alkyl group, a cycloalkyl group, an aryl group, or an aralkyl group, $R^{2c}$ and $R^{2d}$ each may represent a hydrogen atom, $R^{3a}$ and $R^{3b}$ each may represent a hydrogen atom, an alkyl group, a cycloalkyl group, an aryl group, or an aralkyl group, and $R^4$ and $R^5$ each may represent a hydrogen atom or an alkyl group; or $R^4$ and $R^5$ may bond together to form a heterocyclic ring, and the heterocyclic ring may be a 5- to 7-membered heterocyclic ring which may further contain at least one hetero atom selected from the group consisting of a nitrogen atom, an oxygen atom, and a sulfur atom.

In the formula (1), $R^{2a}$, $R^{2b}$, $R^{2c}$, and $R^{2d}$ each may represent a hydrogen atom, $R^{3a}$ and $R^{3b}$ each may represent a hydrogen atom or methyl group, and $R^4$ and $R^5$ each may represent a hydrogen atom or a $C_{1-6}$alkyl group; or $R^4$ and $R^5$ may bond together to form a heterocyclic ring, and the heterocyclic ring may be a pyrrolidine ring, a piperidine ring, a homopiperidine ring, or a morpholine ring.

In the formula (1), $R^4$ and $R^5$ each may represent a hydrogen atom.

The polyamide-series resin may be an aliphatic polyamide resin. A monomer forming or producing the polyamide-series resin may contain an aliphatic monomer with an alkylene group having 4 to 12 carbon atoms. In the resin composition, a mass ratio of the compound represented by the formula (1) relative to the polyamide-series resin may be about 1/99 to 10/90 in terms of the former/the latter.

The resin composition may further contain a fibrous reinforcing material (reinforcing agent). The fibrous reinforcing material may be an inorganic fiber. A ratio of the compound represented by the formula (1) may be about 0.5 to 100 parts by mass relative to 100 parts by mass of the fibrous reinforcing material.

Further, the present disclosure includes a method for improving a fluidity of a polyamide-series resin, which comprises or includes adding a compound represented by the formula (1) to a polyamide-series resin; and a fluidity improving agent, comprising or containing the compound represented by the formula (1).

In this description and claims, the number of carbon atoms in a substituent may be represented as $C_1$, $C_6$, $C_{10}$. For example, an alkyl group having one carbon atom is represented as "$C_1$alkyl group", and an aryl group having 6 to 10 carbon atoms is represented as "$C_{6-10}$aryl group".

Advantageous Effects of Invention

The resin composition of the present disclosure contains a fluorene derivative with a specific chemical structure and a polyamide-series resin, and therefore has an excellent fluidity (specifically, melt fluidity). Moreover, the prepared resin composition can be compatible a mechanical strength such as a flexural strength, a flexural modulus, a tensile strength, and a tensile modulus with a fluidity at a high level in a well-balanced manner. Further, the present disclosure can provide a method for improving the fluidity such as the melt fluidity of the polyamide-series resin by using the fluorene derivative.

BRIEF DESCRIPTION OF DRAWINGS

FIG. 1 is a $^1$H-NMR spectrum of DEAA-FL obtained in Synthesis Example 1.

FIG. 2 is a $^1$H-NMR spectrum of DMAA-FL obtained in Synthesis Example 2.

FIG. 3 is a $^1$H-NMR spectrum of NIPAM-FL obtained in Synthesis Example 3.

FIG. 4 is a $^1$H-NMR spectrum of AAD-FL obtained in Synthesis Example 4.

DESCRIPTION OF EMBODIMENTS

[Fluorene Derivative]

In the present disclosure, the fluorene derivative functioning as a fluidity improving agent (a melt fluidity improving agent) is a compound represented by the following formula (1).

[Chem. 4]

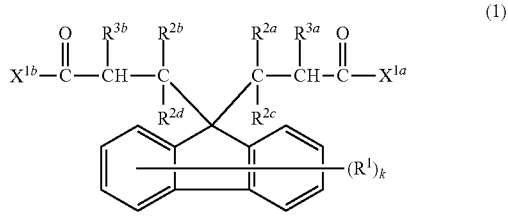

(1)

In the formula (1), $R^1$ represents a substituent, k denotes an integer of 0 to 8, $R^{2a}$, $R^{2b}$, $R^{2c}$, and $R^{2d}$ independently represent, a hydrogen atom or a substituent, $R^{3a}$ and $R^{3b}$ independently represent a hydrogen atom or a substituent, and $X^{1a}$ and $X^{1b}$ independently represent a group defined in the following formula (X1):

[Chem. 5]

(X1)

wherein $R^4$ and $R^5$ independently represent a hydrogen atom or a hydrocarbon group; or $R^4$ and $R^5$ bond together to form a heterocyclic ring containing the nitrogen atom adjacent to $R^4$ and $R^5$.

In the formula (1), the group $R^1$ may be a non-reactive substituent inert or inactive to a reaction, and may include, for example, a cyano group; a halogen atom such as a fluorine atom, a chlorine atom, and a bromine atom; and a hydrocarbon group such as an alkyl group and an aryl group. The aryl group may include a $C_{6-10}$aryl group such as phenyl group. The preferred group $R^1$ includes the cyano group, the halogen atom, or the alkyl group, and particularly the alkyl group.

The alkyl group may include, for example, a $C_{1-12}$alkyl group such as methyl group, ethyl group, n-propyl group, isopropyl group, n-butyl group, and t-butyl group, preferably a $C_{1-8}$alkyl group, and particularly a $C_{1-4}$alkyl group such as methyl group.

In a case where the substitution number k of the groups $R^1$ denotes the plural (2 or more), among the two benzene rings constituting the fluorene ring, the species of the two or more groups $R^1$ bonded to one or the other of the two benzene rings may be the same or different from each other; and the species of the two or more groups $R^1$ bonded to each of the two benzene rings may be the same or different from each other. The bonding position(s) (substitution position(s)) of the group(s) $R^1$ is any one of 1- to 8-positions of the fluorene ring without particular limitation, and may for example be 2-position, 7-position, and 2,7-positions of the fluorene ring.

The substitution number k may for example be an integer of about 0 to 6, and a preferred range of the substitution number k is an integer of 0 to 4, an integer of 0 to 3, and an integer of 0 to 2 in a stepwise manner. The substitution number k is more preferably 0 or 1, and particularly 0. Each substitution number of the groups $R^1$ on the two benzene rings constituting the fluorene ring may be different from each other, and the same substitution numbers are preferred.

The substituent represented by $R^{2a}$, $R^{2b}$, $R^{2c}$, and $R^{2d}$ may be a non-reactive substituent inert or inactive to a reaction, and may include, for example, a hydrocarbon group such as an alkyl group, a cycloalkyl group, an aryl group, and an aralkyl group.

The alkyl group may include, for example, a straight- or branched-chain $C_{1-10}$alkyl group such as methyl group, ethyl group, propyl group, isopropyl group, n-butyl group, isobutyl group, s-butyl group, and t-butyl group. The alkyl group is preferably a straight- or branched-chain $C_{1-6}$alkyl group, and more preferably a straight- or branched-chain $C_{1-4}$alkyl group.

Examples of the cycloalkyl group may include a $C_{5-10}$cycloalkyl group such as cyclopentyl group and cyclohexyl group.

The aryl group may include, for example, a $C_{6-12}$aryl group such as phenyl group, an alkylphenyl group, biphenylyl group, and naphthyl group. Examples of the alkylphenyl group may include a mono- to tri-$C_{1-4}$alkyl-phenyl group such as methylphenyl group (or tolyl group) and dimethylphenyl group (or xylyl group).

The aralkyl group may include, for example, a $C_{6-10}$aryl-$C_{1-4}$alkyl group such as benzyl group and phenethyl group.

The preferred substituent represented by $R^{2a}$, $R^{2b}$, $R^{2c}$, and $R^{2d}$ may include an alkyl group. The alkyl group is preferably a $C_{1-6}$alkyl group, a $C_{1-5}$alkyl group, a $C_{1-4}$alkyl group, and a $C_{1-3}$alkyl group in a stepwise manner, more preferably a $C_{1-2}$alkyl group, and particularly methyl group.

Each of the substituents $R^{2a}$, $R^{2b}$, $R^{2c}$, and $R^{2d}$ preferably represents a hydrogen atom or a hydrocarbon group, more preferably a hydrogen atom or an alkyl group, and further preferably a hydrogen atom. At least $R^{2c}$ and $R^{2b}$ each preferably represent a hydrogen atom; and $R^{2a}$ and $R^{2b}$ each in such an embodiment of $R^{2c}$ and $R^{2d}$ preferably represent a hydrogen atom or a hydrocarbon group, more preferably a hydrogen atom or an alkyl group, and particularly a hydrogen atom (that is, in particularly preferred embodiment, all $R^{2a}$, $R^{2b}$, $R^{2c}$, and $R^{2d}$ represent a hydrogen atom).

The species of the groups $R^{2a}$, $R^{2b}$, $R^{2c}$, and $R^{2d}$ may be different from each other; and the groups $R^{2a}$ and $R^{2b}$ are preferably the same species, and the groups $R^{2c}$ and $R^{2d}$ are preferably the same species.

The substituent represented by $R^{3a}$ and $R^{3b}$ may be a non-reactive substituent inert to a reaction, and may include, for example, a hydrocarbon group such as an alkyl group, a cycloalkyl group, an aryl group, and an aralkyl group. Such a hydrocarbon group may include, for example, the same hydrocarbon groups exemplified as the substituent represented by $R^{2a}$ and $R^{2b}$.

Among the substituents represented by $R^{3a}$ and $R^{3b}$, the preferred substituent is an alkyl group. The alkyl group is preferably a $C_{1-6}$alkyl group, a $C_{1-5}$alkyl group, a $C_{1-4}$alkyl group, and a $C_{1-3}$alkyl group in a stepwise manner, more preferably a $C_{1-2}$alkyl group, and particularly methyl group.

The group represented by $R^{3a}$ and $R^{3b}$ is preferably a hydrogen atom or an alkyl group, more preferably a hydrogen atom or methyl group, and particularly a hydrogen atom.

In the groups $X^{1a}$ and $X^{1b}$ (or formula (X1)), examples of the hydrocarbon group represented by $R^4$ and $R^5$ may include an alkyl group, a cycloalkyl group, an aryl group, an aralkyl group, and a group of a combination of these groups.

The alkyl group may include, for example, a straight- or branched-chain $C_{1-12}$alkyl group such as methyl group, ethyl group, propyl group, isopropyl group, n-butyl group, isobutyl group, s-butyl group, t-butyl group, pentyl group, neopentyl group, hexyl group, octyl group, and decyl group.

Examples of the cycloalkyl group may include a $C_{5-10}$cycloalkyl group such as cyclopentyl group and cyclohexyl group.

The aryl group may include, for example, a $C_{6-12}$aryl group such as phenyl group, an alkylphenyl group, biphenylyl group, and naphthyl group. Examples of the alkylphenyl group may include a mono- to tri-$C_{1-4}$alkyl-phenyl group such as methylphenyl group (or tolyl group) and dimethylphenyl group (or xylyl group).

The aralkyl group may include, for example, a $C_{6-10}$aryl-$C_{1-4}$alkyl group such as benzyl group and phenethyl group.

Among the hydrocarbon groups represented by $R^4$ and $R^5$, the hydrocarbon group is preferably a straight- or branched-chain alkyl group, and more preferably a straight- or branched-chain $C_{1-8}$alkyl group, a straight- or branched-chain $C_{1-6}$alkyl group, and a straight- or branched-chain $C_{1-4}$alkyl group in a stepwise manner, and particularly a straight- or branched-chain $C_{1-3}$alkyl group such as methyl group, ethyl group, and isopropyl group. From a viewpoint of exhibiting higher dispersibility (or compatibility) for a resin, the hydrocarbon group is preferably a straight- or branched-chain $C_{2-4}$alkyl group, and more preferably a straight- or branched-chain $C_{2-3}$alkyl group. In a case where both $R^4$ and $R^5$ represent a hydrocarbon group, the species of $R^4$ and $R^5$ may be different from each other, and the same species are preferred.

The groups $R^4$ and $R^5$ may bond together to form a heterocyclic ring containing the nitrogen atom adjacent to $R^4$ and $R^5$ (N-containing heterocyclic ring or a nitrogen-atom-containing heterocyclic ring); said nitrogen atom, as a hetero atom, forms an amide group (amide bond or carboxyamide) by combining $R^4$, $R^5$ with the carbonyl group; and if necessary, the heterocyclic ring may further contain, in addition to the nitrogen atom, 1 or more hetero atom(s) which may include, for example, a nitrogen atom, an oxygen atom, and a sulfur atom. The heterocyclic ring may contain at least, one additional hetero atom selected from these hetero atoms, and preferably includes at least an oxygen atom. The number of hetero atoms constituting the heterocyclic ring may for example be about 1 to 3, and is preferably 1 to 2, and more preferably 2. Usually, the heterocyclic ring is, for example, a 5- to 7-membered ring (a 5- to 7-membered heterocyclic ring), preferably a 5- or 6-membered ring, and more preferably a 6-membered ring. The heterocyclic ring may be an aromatic heterocyclic ring, and is preferably a nonaromatic heterocyclic ring.

Representative examples of the heterocyclic ring may include a heterocyclic ring containing 1 or more nitrogen atom(s) such as a pyrrolidine ring, a piperidine ring, and a homopiperidine ring fan azepane ring, a hexahydroazepine ring, or hexamethyleneimine ring), and a heterocyclic ring containing a nitrogen atom and a hetero atom different from the nitrogen atom such as a morpholine ring; the heterocyclic ring is preferably a nonaromatic 5- to 7-membered heterocyclic ring containing a nitrogen atom and a hetero atom different from the nitrogen atom (particularly an oxygen atom) such as a morpholine ring.

In the formula (X1), with respect to the groups $R^4$ and $R^5$ adjacent to the nitrogen atom, both $R^4$ and $R^5$ may be a hydrogen atom; one of the groups $R^4$ and $R^5$ may be a hydrogen atom, and the other may be an aliphatic hydrocarbon group; and both $R^4$ and $R^5$ may be an aliphatic hydrocarbon group; or $R^4$ and $R^5$ may bond together to form a heterocyclic ring. That is, a group [—C(=O)—$X^{1a}$] and/or a group [—C(=O)—$X^{1b}$] may be a non-substituted amide group (or a carbamoyl group [—C(=O)—NH$_2$]); a mono-substituted amide group (or a N-substituted amide group); and a di-substituted amide group (or a N,N-disubstituted amide group). The group [—C(=O)—$X^{1a}$] and/or the group [—C(=O)—$X^{1b}$] is preferably the mono-substituted amide group in order to improve a fluidity such as a melt fluidity (hereinafter, is simply referred to as "fluidity", unless otherwise noted), and to effectively improve mechanical characteristics such as a flexural strength, a flexural modulus, a tensile strength, and a tensile modulus in a well-balanced manner. The group [—C(=O)—$X^{1a}$] and/or the group [—C(=O)—$X^{1b}$] is preferably the di-substituted amide group in order to extremely improve solubility in solvents and to improve a fluidity further effectively. In order to achieve mechanical characteristics and a fluidity at an extremely high level, the group [—C(=O)—$X^{1a}$] and/or the group [—C(=O)—$X^{1b}$] is preferably the non-substituted amide group (unsubstituted amide group); and, in particular, it is most preferable that both of the groups [—C(=O)—$X^{1a}$] and [—C(=O)—$X^{1b}$] are the non-substituted amide groups. In the di-substituted amide group, both $R^4$ and $R^5$ are preferably the aliphatic hydrocarbon group. The species of the groups $X^{1a}$ and $X^{1b}$ may be different from each other, and the same species are preferred.

Representative examples of the compound represented by the formula (1) may include a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ represent a hydrogen atom in the formula (1), specifically a 9,9-bis([2-carbamoyl)$C_{2-3}$alkyl]fluorene such as 9,9-bis(2-carbamoylethyl)fluorene and 9,9-bis(2-carbamoylpropyl)fluorene; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and one of $R^4$ and $R^5$ represents a hydrogen atom and the other represents an alkyl group in the formula (1), specifically a 9,9-bis[2-(N—$C_{1-6}$alkyl-carbamoyl)$C_{2-3}$alkyl]fluorene such as 9,9-bis[2-(N-methylcarbamoyl)ethyl]fluorene, 9,9-bis[2-(N-methylcarbamoyl)propyl]fluorene, 9,9-bis[2-(N-ethylcarbamoyl)ethyl]fluorene, 9,9-bis[2-(N-isopropylcarbamoyl)ethyl]fluorene, 9,9-bis[2-(N-isopropylcarbamoyl)propyl]fluorene, and 9,9-bis[2-(N-butylcarbamoyl)ethyl]fluorene; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and each of $R^4$ and $R^5$ represents an alkyl group in the formula (1), specifically a 9,9-bis[2-(N,N-di$C_{1-6}$alkyl-carbamoyl)$C_{2-3}$alkyl]fluorene such as 9,9-bis[2-(N,N-dimethylcarbamoyl)ethyl]fluorene, 9,9-bis[2-(N,N-dimethylcarbamoyl)propyl]fluorene, 9,9-bis[2-(N,N-diethylcarbamoyl)ethyl]fluorene, 9,9-bis[2-(N,N-diethylcarbamoyl)propyl]fluorene, 9,9-bis[2-(N,N-diisopropylcarbamoyl)ethyl]fluorene, and 9,9-bis[2-(N,N-dibutylcarbamoyl)ethyl]fluorene; and a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and $R^4$ and $R^5$ bond together to form a 5- to 7-membered heterocyclic ring which may further contain, in addition to the nitrogen atom constituting an amide group, at least one hetero atom selected from the group consisting of a nitrogen atom, an oxygen atom, and a sulfur atom in the formula (1), specifically a 9,9-bis[2-(N-containing heterocyclic ring-N-yl-carbonyl)$C_{2-3}$alkyl]fluorene such as 9,9-bis[2-(morpholine-4-yl-carbonyl)ethyl]fluorene, 9,9-bis[2-(morpholine-4-yl-carbonyl)propyl]fluorene, 9,9-bis[2-(pyrrolidine-1-yl-carbonyl)ethyl]fluorene, 9,9-bis[2-(piperidine-1-yl-carbonyl)ethyl]fluorene, and 9,9-bis[2-(homopiperidine-1-yl-carbonyl)ethyl]fluorene.

These fluorene derivatives may be used alone or in combination of two or more. Among these fluorene derivatives, the preferred fluorene derivatives are a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ in the groups $X^{1a}$ and $X^{1b}$ represent a hydrogen atom in the formula (1) (non-substituted amide compound); a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and one of the groups $R^4$ and $R^5$ in the groups $X^{1a}$ and $X^{1b}$ represents a hydrogen atom and the other represents an alkyl group in the formula (1) (N-alkyl substituted compound); and a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ in the groups $X^{1a}$ and $X^{1b}$ represent an alkyl group in the formula (1) (N,N-dialkyl substituted compound). Among such fluorene derivatives, the preferred fluorene derivative is the N-alkyl substituted compound such as a 9,9-bis[2-(N—$C_{1-4}$alkyl-carbamoyl)$C_{2-3}$alkyl]fluorene, and particularly a 9,9-bis[2-(N—$C_{2-4}$alkyl-carbamoyl)$C_{2-3}$alkyl]fluorene such as 9,9-bis[2-(N-isopropylcarbamoyl)ethyl]fluorene in order to improve the fluidity, and to effectively improve mechanical characteristics such as the flexural strength, the flexural modulus, the tensile strength, and the tensile modulus in a well-balanced manner. The preferred fluorene derivative is the N,N-dialkyl substituted compound such as a 9,9-bis[2-(N,N-di$C_{1-4}$alkyl-carbamoyl)$C_{2-3}$alkyl]fluorene, more preferably a 9,9-bis[2-(N,N-di$C_{1-3}$alkyl-carbamoyl)$C_{2-3}$alkyl]fluorene such as 9,9-bis[2-(N,N-dimethylcarbamoyl)ethyl]fluorene and 9,9-bis[2-(N,N-diethylcarbamoyl)ethyl]fluorene, and particularly 9,9-bis[2-(N,N-diethylcarbamoyl)ethyl]fluorene in order to extremely improve a solubility in a wide variety of solvents, and to further effectively improve the fluidity. In order to achieve the mechanical characteristics and the fluidity at a higher level, the fluorene derivative is most preferably the non-substituted amide compound over the N-alkyl substituted compound and N,N-dialkyl substituted compound, and particularly a 9,9-bis(2-carbamoyl)$C_{2-3}$alkyl)fluorene such as 9,9-bis(2-carbamoylethyl)fluorene and 9,9-bis(2-carbamoylpropyl)fluorene.

[Method for Producing Fluorene Derivative]

The method for producing a compound represented by the formula (1) is not particularly limited to a specific method, and may for example be prepared by reacting a compound represented by the following formula (2) with compounds represented by the following formulae (3a) and (3b) (Michael addition reaction).

[Chem. 6]

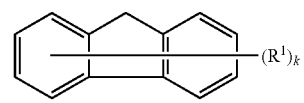

(2)

In the formula (2), $R^1$ and k, including preferred embodiments, each have the same meanings as defined in the formula (1).

[Chem. 7]

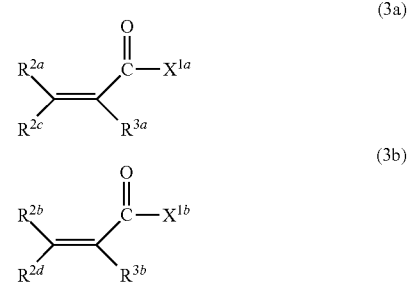

In the formulae (3a) and (3b), $R^{2a}$, $R^{2b}$, $R^{2c}$, and $R^{2d}$, $R^{3a}$ and $R^{3b}$, and $X^{1a}$ and $X^{1b}$, including preferred embodiments, each have the same meanings as defined in the formula (1).

Representative examples of the compound represented by the formula (2) may include 9H-fluorene.

Each of the compounds represented by the formulae (3a) and (3b) may be either E-isomer or Z-isomer depending on the species or kinds of the groups $R^{2a}$, $R^{2b}$, $R^{2c}$, and $R^{2d}$, $R^{3a}$ and $R^{3b}$, and $X^{1a}$ and $X^{1b}$.

Representative compounds represented by the formulae (3a) and (3b), for example, correspond to a compound specifically exemplified as the compound represented by the formula (1), and may include a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ represent a hydrogen atom, specifically, for example, a compound such as (moth)acrylamide; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and one of the groups $R^4$ and $R^5$ represents a hydrogen atom and the other represents an alkyl group, specifically, for example, a N—$C_{1-6}$alkyl-(meth)acrylamide such as N-isopropyl(meth)acrylamide; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and both $R^4$ and $R^5$ represent an alkyl group, specifically, for example, a N,N-di$C_{1-6}$alkyl-(meth)acrylamide such as N,N-dimethyl(meth)acrylamide and N,N-diethyl(meth)acrylamide; a compound in which each of $R^{2a}$, $R^{2b}$, $R^{2c}$, and $R^{2d}$ represents a hydrogen atom, each of $R^{3a}$ and $R^{3b}$ represents a hydrogen atom or methyl group, and $R^4$ and $R^5$ bond together to form a 5- to 7-membered heterocyclic ring which may further contain, in addition to the nitrogen atom constituting an amide group, at least one hetero atom selected from the group consisting of a nitrogen atom, an oxygen atom, and a sulfur atom, specifically, for example, a N-(meth)acryloyl N-containing heterocyclic ring such as N-(meth)acryloylmorpholine. The same compound is preferably used as the compound represented by the formula (3a) and the compound represented by the formula (3b).

The amount of the compound represented by the formula (2) relative to the total amount of the compounds represented by the formulae (3a) and (3b) may for example be a molar ratio of about 1/2 to 1/10 in terms of the former/the latter; and a preferred range of the molar ratio is, in terms of the former/the latter, 1/2 to 1/5, 1/2.01 to 1/3, and 1/2.03 to 1/2.1 in a stepwise manner.

The reaction may usually be carried out in the presence of a base. The base may include, for example, a metal hydroxide, a metal carbonate or bicarbonate (hydrogen carbonate), and a metal alkoxide.

Examples of the metal hydroxide may include an alkali metal hydroxide such as sodium hydroxide and potassium hydroxide; and an alkaline earth metal hydroxide such as barium hydroxide.

Examples of the metal carbonate or bicarbonate may include an alkali metal carbonate or bicarbonate such as sodium carbonate, potassium carbonate, and sodium bicarbonate (sodium hydrogen carbonate).

Examples of the metal alkoxide may include an alkali metal alkoxide such as sodium methoxide, sodium ethoxide, and potassium t-butoxide.

These bases may be used alone or in combination of two or more. Among these bases, the base is preferably the metal hydroxide, and more preferably the alkali metal hydroxide such as potassium hydroxide. The ratio of the bases may for example be about 0.001 to 0.1 mol, and is preferably 0.01 to 0.05 mol relative to 1 mol of the compound represented by the formula (2).

The reaction may be carried out in the presence or absence of phase transfer catalyst(s). The phase transfer catalyst may include, for example, a tetraalkylammonium halide such as tetrabutylammonium bromide (TBAB) and trioctylmethylammonium chloride. These phase transfer catalysts may be used alone or in combination of two or more. Among these phase transfer catalysts, TBAB is preferred. The ratio of the phase transfer catalysts may for example be about 0.001 to 0.1 mol, and is preferably 0.01 to 0.05 mol relative to 1 mol of the compound represented by the formula (2).

The reaction may be carried out in the absence or presence of an inert, or inactive solvent to a reaction. Examples of the solvent may include water; an alcohol such as methanol and ethanol; an ether such as a cyclic ether and a chain ether; a sulfoxide such as dimethyl sulfoxide (DMSO); and a hydrocarbon such as an aliphatic hydrocarbon, an alicyclic hydrocarbon, and an aromatic hydrocarbon.

Examples of the cyclic ether may include 1,4-dioxane and tetrahydrofuran. Examples of the chain ether may include a dialkyl ether such as diethyl ether and diisopropyl ether; and a glycol ether. The glycol ether may include, for example, a (poly)alkylene glycol monoalkyl ether such as methyl cellosolve and methyl carbitol; and a (poly)alkylene glycol dialkyl ether such as dimethoxyethane.

Examples of the aliphatic hydrocarbon may include hexane and dodecane. The alicyclic hydrocarbon may include cyclohexane. The aromatic hydrocarbon may include, for example, toluene and xylene.

These solvents may be used alone or in combination of two or more. Among these solvents, the preferred solvent is a mixed solvent of water, the sulfoxide such as DMSO, and the aromatic hydrocarbon such as toluene. The water may be added in the form of an aqueous solution of the base described above. The amount of the solvents is not particularly limited to a specific amount as long as the progress of the reaction is not interfered. The amount of the solvents may for example be about 10 to 500 mL, and is preferably 50 to 200 mL relative to 100 g of the total amount of the compounds represented by the formulae (2), (3a), and (3b).

The reaction may be carried out in an atmosphere of an inert gas such as a nitrogen gas; and a rare or noble gas such as helium and argon. The reaction temperature is, for example, 50 to 200° C., and preferably 80 to 100° C. The reaction time is not particularly limited to a specific time, and may for example be about 0.5 to 10 hours.

After the completion of the reaction, if necessary, the reaction mixture may be subjected to a conventional separation and purification means, for example, a method such as neutralization, washing, extraction, filtration, decantation, concentration, dehydration, drying, crystallization, and chromatography and a combination of these methods.

(Characteristics)

The fluorene derivative obtained as described above may be in a crystalline or amorphous form. In a crystalline fluorene derivative, the fluorene derivative in which the groups [—C(=O)—$X^{1a}$] and [—C(=O)—$X^{1b}$] each are the non-substituted amide group, may have a melt point of, for example, about 200 to 300° C., and the melting point is preferably 230 to 280° C., and more preferably 240 to 270° C.; the fluorene derivative in which the groups [—C(=O)—$X^{1a}$] and [—C(=O)—$X^{1b}$] each are the mono-substituted amide group, may have a melt point of, for example, about 150 to 300° C., and the melting point is preferably 200 to 270° C., and more preferably 220 to 250° C.; and the fluorene derivative in which the groups [—C(=O)—$X^{1a}$] and [—C(=O)—$X^{1b}$] each are the di-substituted amide group, may have a melt point of, for example, about 50 to 200° C., and the melting point is preferably 70 to 180° C., and more preferably 80 to 160° C.

Further, a 5% mass reduction temperature of the fluorene derivative may for example be about 200 to 400° C., and is preferably 230 to 380° C., 230 to 360° C., 280 to 350° C., 300 to 340° C., and 310 to 330° C. in a stepwise manner. The fluorene derivative has a high heat resistance as described above. Therefore, even in a high-temperature environment, the fluorene derivative can be effectively used as a fluidity improving agent or a strength improving agent.

The fluorene derivative has an excellent solubility in solvents. In particular, a compound (the fluorene derivative) in which the group [—C(=O)—$X^{1a}$] and/or [—C(=O)—$X^{1b}$] are the di-substituted amide group in the formula (1) tends to be more soluble in more variety of solvents.

In this description and claims, the melting point, the 5% mass reduction temperature, and the solubility in solvents can be measured according to the methods described in Examples mentioned below.

[Polyamide-Series Resin]

As a polyamide-series resin (PA) contained in a resin composition, a conventional polyamide-series resin can be used. The polyamide-series resin may for example be formed with an aliphatic monomer component, an alicyclic monomer component, and/or an aromatic monomer component.

In this description and claims, a monomer component having a carboxyl group such as dicarboxylic acid described later, may be an amide-forming derivative, for example, an acid halide such as an acid chloride, and an acid anhydride.

The aliphatic monomer component may include, for example, an aliphatic diamine component, an aliphatic dicarboxylic acid component, an aliphatic aminocarboxylic acid component, and a lactam component.

The aliphatic diamine component may include, for example, a straight- or branched-chain $C_{2-20}$alkylene diamine such as tetramethylene diamine, hexamethylene diamine, 2-methyl pentamethylene diamine, nonamethylene diamine, 2-methyl octamethylene diamine, trimethyl hexamethylene diamine, decamethylene diamine, and dodecamethylene diamine, and is preferably a straight- or branched-chain $C_{4-16}$alkylene diamine, and more preferably a straight- or branched-chain $C_{6-12}$-alkylene diamine.

Examples of the aliphatic dicarboxylic acid component may include a saturated aliphatic dicarboxylic acid (a straight- or branched-chain alkane dicarboxylic acid) and an unsaturated aliphatic dicarboxylic acid.

The straight- or branched-chain alkane dicarboxylic acid may include, for example, a straight- or branched-chain $C_{1-20}$alkane-dicarboxylic acid such as malonic acid, succinic acid, glutaric acid, adipic acid, pimelic acid, suberic acid, azelaic acid, sebacic acid, and 1,10-decane dicarboxylic acid, and is preferably a straight- or branched-chain $C_{2-16}$alkane-dicarboxylic acid, and more preferably a straight- or branched-chain $C_{4-12}$alkane-dicarboxylic acid such as adipic acid, sebacic acid, and 1,10-decane dicarboxylic acid.

The unsaturated aliphatic dicarboxylic acid may include, for example, a $C_{2-10}$alkene-dicarboxylic acid such as maleic acid, fumaric acid, and itaconic acid.

The aliphatic aminocarboxylic acid component may include, for example, an amino$C_{2-20}$alkyl-carboxylic acid such as 6-aminohexanoic acid, 11-aminoundecanoic acid, and 12-aminododecanoic acid, and is preferably an amino$C_{3-16}$alkyl-carboxylic acid, and more preferably an amino$C_{5-11}$alkyl-carboxylic acid.

The lactam component may be a lactam corresponding to the aliphatic aminocarboxylic acid; and may include, for example, a 4- to 13-membered ring lactam such as ε-caprolactam and ω-laurolactam, and preferably a 7- to 13-membered ring lactam.

The alicyclic monomer component has an alicyclic skeleton (or an aliphatic hydrocarbon ring skeleton), and may include, for example, an alicyclic diamine component, an alicyclic dicarboxylic acid component, and an alicyclic aminocarboxylic acid component.

Examples of the alicyclic diamine component may include a diaminocycloalkane, bis(aminoalkyl)cycloalkane, and bis(aminocyclohexyl)alkane.

The diaminocycloalkane may include, for example, a diamino$C_{5-10}$cycloalkane such as diaminocyclohexane.

The bis(aminoalkyl)cycloalkane may include, for example, a bis(amino$C_{1-4}$alkyl)$C_{5-10}$cycloalkane such as bis(aminomethyl)cyclohexane.

The bis(aminocyclohexyl)alkane may include, for example, a bis(aminocyclohexyl)$C_{1-6}$alkane such as bis(4-aminocyclohexyl)methane and 2,2-bis(4-aminocyclohexyl)propane; a bis(amino-mono- to tri-$C_{1-6}$alkyl-$C_{5-10}$cycloalkyl)$C_{1-6}$alkane such as bis(4-amino-3-methylcyclohexyl)methane, bis(4-amino-3,5-dimethylcyclohexyl)methane, and 2,2-bis(4-amino-3-methylcyclohexyl)propane.

Examples of the alicyclic dicarboxylic acid component may include a cycloalkanedicarboxylic acid, a bridged ring (crosslinked ring) cycloalkanedicarboxylic acid, a cycloalkenedicarboxylic acid, and a bridged ring (crosslinked-ring) cycloalkenedicarboxylic acid.

The cycloalkanedicarboxylic acid may include, for example, a $C_{5-10}$cycloalkane-dicarboxylic acid such as 1,4-cyclohexanedicarboxylic acid.

The bridged ring cycloalkanedicarboxylic acid may include, for example, a bi- or tri-cycloalkanedicarboxylic acid such as decalindicarboxylic acid, norbornanedicarboxylic acid, adamantanedicarboxylic acid, and tricyclodecanedicarboxylic acid.

The cycloalkenedicarboxylic acid may include, for example, a $C_{5-10}$cycloalkene-dicarboxylic acid such as cyclohexenedicarboxylic acid.

The bridged ring cycloalkenedicarboxylic acid may include, for example, a bi- or tri-cycloalkenedicarboxylic acid such as norbornenedicarboxylic acid.

The alicyclic aminocarboxylic acid component may include, for example, an aminocycloalkanecarboxylic acid, specifically an amino$C_{5-10}$cycloalkane-carboxylic acid such as aminocyclohexanecarboxylic acid.

The aromatic monomer component has an aromatic ring skeleton. As examples of the aromatic monomer component, there may be mentioned an aromatic (or araliphatic) diamine component, an aromatic (or araliphatic) dicarboxylic acid component, and an aromatic (or araliphatic) aminocarboxylic acid component.

Examples of the aromatic (or araliphatic) diamine component may include a diaminoarene and a bis(aminoalkyl)arene. The diaminoarene may include, for example, a diamino$C_{6-14}$arene such as m-phenylenediamine, p-phenylenediamine, and m-xylylenediamine. The bis(aminoalkyl)arene may include, for example, a bis(amino$C_{1-4}$alkyl)arene such as m-xylylenediamine.

Examples of the aromatic (or araliphatic) dicarboxylic acid component may include a benzene dicarboxylic acid, an alkylbenzene dicarboxylic acid, a polycyclic arene dicarboxylic acid, a diarylalkane dicarboxylic acid, a diarylketone dicarboxylic acid, a diarylether dicarboxylic acid, a diarylsulfide dicarboxylic acid, and a diarylsulfone dicarboxylic acid.

The benzene dicarboxylic acid may include, for example, phthalic acid, isophthalic acid, and terephthalic acid. The alkylbenzene dicarboxylic acid may include, for example, a $C_{1-4}$alkyl-benzene dicarboxylic acid such as 4-methylisophthalic acid and 5-methylisophthalic acid.

The polycyclic arene dicarboxylic acid may include, for example, a condensed polycyclic arene dicarboxylic acid and a ring-assemblies (or ring-aggregated) arene dicarboxylic acid.

Examples of the condensed polycyclic arene dicarboxylic acid may include a condensed polycyclic $C_{10-24}$arene-dicarboxylic acid such as a naphthalenedicarboxylic acid, e.g., 1,2-naphthalenedicarboxylic acid, 1,4-naphthalenedicarboxylic acid, 1,5-naphthalenedicarboxylic acid, 1,8-naphthalenedicarboxylic acid, 2,3-naphthalenedicarboxylic acid, 2,6-naphthalenedicarboxylic acid, and 2,7-naphthalenedicarboxylic acid; an anthracenedicarboxylic acid; and a phenanthrenedicarboxylic acid; and preferably a condensed polycyclic $C_{10-14}$arene-dicarboxylic acid.

Examples of the ring-assemblies arene dicarboxylic acid may include a bi$C_{6-10}$arene-dicarboxylic acid such as 2,2'-biphenyldicarboxylic acid, 3,3'-biphenyldicarboxylic acid, and 4,4'-biphenyldicarboxylic acid.

Examples of the diarylalkane dicarboxylic acid may include a di$C_{6-10}$aryl$C_{1-6}$alkane-dicarboxylic acid such as 4,4'-diphenylmethane dicarboxylic acid.

Examples of the diarylketone dicarboxylic acid may include a di($C_{6-10}$aryl) ketone-dicarboxylic acid such as 4,4'-diphenylketone dicarboxylic acid.

Examples of the diarylether dicarboxylic acid may include a di($C_{6-10}$aryl)ether-dicarboxylic acid such as 4,4'-diphenylether dicarboxylic acid.

Examples of the diarylsulfide dicarboxylic acid may include a di($C_{6-10}$aryl) sulfide-dicarboxylic acid such as 4,4'-diphenylsulfide dicarboxylic acid.

Examples of the diarylsulfone dicarboxylic acid may include a di($C_{6-10}$aryl) sulfone-dicarboxylic acid such as 4,4'-diphenylsulfone dicarboxylic acid.

The aromatic aminocarboxylic acid component may include, for example, an aminoarene carboxylic acid. The aminoarene carboxylic acid may include, for example, an amino$C_{6-12}$arene carboxylic acid such as aminobenzoic acid.

These monomer components may be used alone or in combination of two or more for producing the polyamide-series resin. For example, the polyamide-series resin may be formed or produced by polymerizing the diamine component and the dicarboxylic acid component; the aminocarboxylic acid component and/or the lactam component; and the diamine component and the dicarboxylic acid component, and the aminocarboxylic acid component and/or the lactam component. The polyamide-series resin may be a homopolyamide formed with a single monomer component (set of a single diamine component and a single dicarboxylic acid component, a single aminocarboxylic acid component, or a single lactam component); and a copolyamide obtained or produced by copolymerizing a plurality of monomer components. Representative examples of the polyamide-series resin may include an aliphatic polyamide resin, an alicyclic polyamide resin, and an aromatic polyamide resin.

The aliphatic polyamide resin comprises an aliphatic monomer unit derived from the aliphatic monomer component, and may include, for example, a homopolyamide of the aliphatic diamine component and the aliphatic dicarboxylic acid component, such as polyamide 46, polyamide 66, polyamide 610, and polyamide 612; a homopolyamide of the aliphatic aminocarboxylic acid component, and/or the lactam component corresponding to the aliphatic aminocarboxylic acid component, such as polyamide 6, polyamide 11, and polyamide 12; a copolymer (copolyamide) of a plurality of aliphatic monomer components, such as copolyamide 6/66, copolyamide 6/11, and copolyamide 66/12.

The alicyclic polyamide resin has an alicyclic monomer unit derived from the alicyclic monomer component, and may be formed with a combination of the aliphatic monomer component and the alicyclic monomer component. Representative examples of the alicyclic polyamide resin may include a homopolyamide of the alicyclic diamine component and the aliphatic dicarboxylic acid component, such as a polymer of diaminomethylcyclohexane and adipic acid.

The aromatic polyamide resin has at least an aromatic monomer unit derived from the aromatic monomer component, and may include, for example, a semiaromatic polyamide resin formed with the aromatic monomer component, and the aliphatic or alicyclic monomer component; a wholly aromatic polyamide resin or a fully aromatic polyamide resin, which is formed by the aromatic monomer component without the aliphatic monomer component and the alicyclic monomer component.

The semiaromatic polyamide resin may include, for example, a homopolyamide of the aromatic (or araliphatic) diamine component and the aliphatic dicarboxylic acid component, such as polyamide MXD 6 (a polymer of m-xylylenediamine and adipic acid); a homopolyamide of the aliphatic diamine component and the aromatic dicarboxylic acid component, such as polyamide 6T (a polymer of hexamethylenediamine and terephthalic acid), polyamide 9T (a polymer of nonamethylene diamine and terephthalic acid), polyamide 10T (a polymer of decamethylene diamine and terephthalic acid), polyamide 12T (a polymer of dodecamethylene diamine and terephthalic acid), polyamide M5T (a polymer of 2-methylpentamethylene diamine and terephthalic acid), polyamide M8T (a polymer of 2-methyloctamethylene diamine and terephthalic acid), polyamide 6I (a polymer of hexamethylenediamine and isophthalic acid), and a polymer of trimethylhexamethylene diamine and terephthalic acid; a copolymer formed with at least the aliphatic diamine component and the aromatic dicarboxylic acid component, such as copolyamide 6T/66, copolyamide 6T/M5T, copolyamide 6T/6I, copolyamide 6T/6I/6, and copolyamide 6T/6I/66.

The wholly aromatic polyamide resin may include, for example, a homopolyamide of the aromatic diamine component and the aromatic dicarboxylic acid component, such as a polymer of m-phenylenediamine and isophthalic acid, and a polymer of p-phenylenediamine and terephthalic acid.

In this description and claims, the symbol "/" for the copolyamide means that the copolyamide comprises the former and latter monomers (units) with respect to the symbol "/" as a copolymerization component (copolymerization unit). That is, copolyamide 6/66 means a copolymer containing a unit producing polyamide 6 and a unit producing polyamide 66.

The polyamide resin may be a polyamide with a N-alkoxymethyl group, and a polymerized fatty acid-series polyamide resin formed with a dimer acid which is a dimer of an unsaturated higher fatty acid as a polymerization component. The polyamide resin may be crystalline or amorphous. Further, the polyamide resin may be a transparent polyamide resin (amorphous transparent polyamide resin). From a viewpoint of mechanical characteristics of a molded article or a molded object, the polyamide resin is preferably a crystalline resin.

These polyamide-series resins may be used alone or in combination of two or more. Among these polyamide-series resins, the aliphatic polyamide resin is preferred. The polyamide-series resin is preferably formed with a monomer comprising the aliphatic monomer component with an alkylene group, the number of carbon atoms of the alkylene group being about 4 to 12, preferably 6 to 11, more preferably 6 to 9, and the polyamide-series resin has particularly at least, alkylene group with 6 carbon atoms. In particular, the polyamide-series resin is preferably the aliphatic polyamide resin formed with the aliphatic monomer component(s) having an alkylene group with the above-mentioned carbon atoms. Representative preferred aliphatic polyamide resin is a homopolyamide of the aliphatic diamine component and the aliphatic dicarboxylic acid component, such as polyamide 46, polyamide 66, polyamide 610, and polyamide 612.

The number average molecular weight Mn of the polyamide-series resin is for example 7000 to 1000000, and a preferred range of Mn is 10000 to 750000, 20000 to 500000, 30000 to 500000, and 50000 to 500000 in a stepwise manner. The molecular weight can be for example measured by a conventional, means such as gel permeation chromatography (GPC) and other means, and may be evaluated or measured as a molecular weight in terms of polystyrene.

[Resin Composition]

A resin composition contains at least the fluorene derivative represented by the formula (1) and the polyamide-series resin. A fluidity of the resin composition, particularly a melt fluidity, can be improved more effectively by adding or using, as an additive, the fluorene derivative represented by the formula (1) to the polyamide-series resin to form the resin composition (thermoplastic resin composition). Further, the improvement of the fluidity of the resin composition can also improve a moldability (processability) thereof. That is, it is conceivably effective to raise the molding temperature (processing temperature) for increasing the fluidity. However, the polyamide-series resin tends to have a relatively low decomposition temperature, for example, the decomposition temperature of a crystalline polyamide-series resin is usually close to a melting point thereof, and therefore there is a limit to increase the fluidity with raising the molding temperature. Furthermore, since the polyamide-series resin tends to have a large temperature dependence of a viscosity as well as a low decomposition temperature, strict temperature control is required to prevent or suppress a thermal decomposition and stabilize the fluidity, but the temperature control becomes more difficult as the molding temperature becomes higher. Thus, the resin composition of the present disclosure, which can improve the fluidity without increasing the molding temperature, is particularly useful.

Despite being a low-molecule weight compound, the fluorene derivative represented by the formula (1) unexpectedly prevents or suppresses the deterioration of the mechanical characteristics of the resin composition, and may even be able to maintain or improve the mechanical characteristics thereof.

(Fibrous Reinforcing Material)

From a viewpoint of mechanical characteristics such as a flexural strength, a flexural modulus, a tensile strength, and a tensile modulus, the resin composition, if necessary, may contain a fibrous reinforcing material (a fibrous reinforcement or a fibrous filler). Although the fibrous reinforcing material generally can greatly improve the mechanical characteristics of a resin composition, a viscosity thereof unavoidably significantly increases. Therefore, it is difficult to be compatible the mechanical characteristics with fluidity (moldability or processability). In particularly, in applications the mechanical characteristics are required, though it is necessary to add much amount of the fibrous reinforcing material to a resin composition, the viscosity of the resin composition becomes remarkably high with increasing the amount of the fibrous reinforcing material, and thus there is no choice to sacrifice the fluidity (moldability or processability). However, according to the present disclosure, the combination of a specific fluorene derivative, a polyamide-series resin, with a fibrous reinforcing material can effectively improve the fluidity of the resin composition even if the fibrous reinforcing material is incorporated. Moreover, despite of containing the low-molecular weight compound (the fluorene derivative), the resin composition can be unexpectedly effectively prevented from the deterioration of high mechanical characteristics due to the fibrous reinforcing material, and it is possible to, in some cases, maintain or improve the mechanical characteristics of the resin composition. Therefore, the resin composition can be easily compatible high mechanical characteristics with high fluidity at a high level. In particular, the resin composition in which the fluorene derivative is incorporated with the fibrous reinforcing material, can easily maintain an impact strength, and is compatible an impact resistance with the fluidity compared with the resin composition which does not contain the fibrous reinforcing material (that is, the resin composition which does not contain the fibrous reinforcing material and has the same mass ratio of the fluorene derivative relative to the polyamide-series resin).

The fibrous reinforcing material may include an organic fiber and an inorganic fiber. Examples of the organic fiber may include a modified or unmodified cellulose fiber (a fiber of a cellulose or a derivative thereof) such as a cellulose fiber and a cellulose acetate fiber; a polyester fiber such as a polyalkylene arylate fiber. Examples of the inorganic fiber may be a glass fiber, a carbon fiber, a boron fiber, a wollastonite, and a metal fiber such as a whisker. The carbon fiber way include, for example, a polyacrylonitrile (PAN)-based carbon fiber; a pitch-based carbon fiber such as an isotropic pitch-based carbon fiber and a mesophase pitch-based carbon fiber; and a vapor grown carbon fiber.

These fibrous reinforcing materials may be used alone or in combination of two or more. The preferred fibrous reinforcing material is the modified or unmodified cellulose fiber and the inorganic fiber, more preferably the inorganic fiber, further preferably the glass fiber and the carbon fiber, and particularly the glass fiber.

The glass component forming the glass fiber may include, for example, an E-glass (no-alkali glass for electrical insulation), S-glass (high-strength glass), C-glass (chemical glass), A-glass (general purpose alkali glass), and YM-31-A glass (high elasticity glass). Among these glass components, from a viewpoint of mechanical characteristics, E-glass, C-glass, and S-glass are preferred, and particularly E-glass. The glass fiber formed by these glass components may be used alone or in combination of two or more.

The fibrous reinforcing material may be used in a form of either a short fiber or a long fiber according to applications or other factors, and the fibrous reinforcing material may be used in the form of a fabric such as a woven fabric, a knit fabric, and a nonwoven fabric. These fibrous reinforcing materials may be used alone or in combination of two or more. From a viewpoint of effectively improving the fluidity, the fibrous reinforcing material is preferably the short fiber.

The fibrous reinforcing material may have an average fiber length (in case of the fabric, an average fiber length of the fiber constituting the fabric) selected from a range of about 0.1 to 10 mm; and a preferred range of the average fiber length is preferably 0.2 to 8 mm, 0.5 to 6 mm, and 1 to 4 mm in a stepwise manner. Further, under an influence of shearing force in mixing (kneading) in preparing a resin composition and in a molding process, the average fiber length of the fibrous reinforcing material in the composition or the molded article (molded object) may be shorter than that before mixing, and is for example be 0.05 to 5 mm, preferably 0.1 to 3 mm, and more preferably 0.2 to 1 mm.

The fibrous reinforcing material may have an average fiber diameter (a filament diameter) on the order of nanometers. Such a fibrous reinforcing material may include, for example, a modified or unmodified cellulose nanofiber, a carbon nanotube, a carbon nanocoil, and a carbon nanofiber. From a viewpoint of a mechanical strength or other factors, the average fiber diameter (the filament diameter) may be on the order of micrometers, and may be selected from a range of about 1 to 200 μm; and the average fiber diameter is preferably 3 to 100 μm, more preferably 4 to 30 μm, and particularly 5 to 15 μm.

Examples of the cross section of the fibrous reinforcing material may include a circular-form, an oval or elliptical-form, and a polygonal-form. The fibrous reinforcing material may be subjected to a conventional surface treatment, and specifically treated with a surface treatment agent such as a sizing agent, and a silane coupling agent.

In the resin composition, a mass ratio of the compound represented by the formula (1) (the fluorene derivative) relative to the polyamide-series resin may for example be selected from a range of about 0.01/95.99 to 50/50 in terms of the former/the latter, and a preferred range of the mass ratio is, in terms of the former/the latter, 0.1/99.9 to 30/70, 0.5/99.5 to 20/30, 1/99 to 15/85, 1/99 to 10/90, 2/98 to 8/92, 3/97 to 7/93, and 4/96 to 6/54 in a stepwise manner. In a case where the resin composition contains the fibrous reinforcing material, the above-mentioned mass ratio is, in terms of the former/the latter, preferably 1/99 to 10/90, 2/98 to 8/92, 2.5/97.5 to 6/94, and 3/97 to 5/95 in a stepwise manner. An excessively higher ratio of the fluorene derivative represented by the formula (1) may provide a possibility to significantly reduce or decrease mechanical characteristics such as the impact resistance of the resin composition to bleed out the fluorene derivative; and an excessively lower ratio of the fluorene derivative represented by the formula (1) may provide a possibility not to improve the fluidity and the mechanical characteristics such as flexural characteristics and tensile characteristics of the resulting resin composition. However, according to the present disclosure, even if the ratio of the fluorene derivative represented by the formula (1) is relatively low, the fluidity of the resin composition can be effectively improved. In particular, when the fluorene derivative is the non-substituted or unsubstituted amide compound, the fluidity of the resin composition cars be further effectively improved without significantly reducing or decreasing, while rather improving mechanical characteristics such as the flexural strength, the flexural modulus, the tensile strength and the tensile modulus.

The mass ratio (the mass ratio of the fluorene derivative relative to the polyamide-series resin) may be selected according to applications. For example, in applications where a high fluidity is especially required, a preferred range of the mass ratio is, in terms of the former/the latter, 4/96 to 15/85, 4/96 to 10/90, and 4.5/95.5 to 6/94 in a stepwise manner; in applications where the balance between the fluidity and the impact resistance is required, a preferred range of the mass ratio is, in terms of the former/the latter, 0.5/99.5 to 4/96, 1/99 to 3.5/96.5, and 2/98 to 3.5/96.5 in a stepwise manner. When the ratio of the fluorene derivative is excessively low, it may be difficult to improve the fluidity of the resin composition, and it may be difficult to improve mechanical, characteristics or properties thereof such as flexural properties and tensile properties; and when the ratio of the fluorene derivative is excessively high, it may be difficult to improve the fluidity of the resin composition while effectively maintaining or improving the impact resistance, and it may be difficult to suppress or prevent the fluorene derivative from bleeding out.

In a case where the resin composition contains the fibrous reinforcing material, the mass ratio of the total amount of the fluorene derivative represented by the formula (1) and polyamide-series resin relative to the fibrous reinforcing material may be for example selected from a range of about 99/1 to 20/80 in terms of the former/the latter; and a preferred range of the mass ratio is, in terms of the former/the latter, 90/10 to 30/70, 80/20 to 35/65, 70/30 to 40/60, 60/40 to 45/55, and 55/45 to 45/55 in a stepwise manner. An excessively lower ratio of the fibrous reinforcing material may adversely affect the improvement of the mechanical characteristics, and an excessively higher ratio of the fibrous reinforcing material may adversely affect the effective improvement of the fluidity.

In a case where the resin composition contains the fibrous reinforcing material, the ratio of the fluorene derivative represented by the formula (1) may for example be about 0.01 to 10000 parts by mass relative to 100 parts by mass of the fibrous reinforcing material, and is preferably 0.1 to 1000 parts by mass, 0.5 to 100 parts by mass, 1 to 50 parts by mass relative to 3.00 parts by mass of the fibrous reinforcing material in a stepwise manner. From a viewpoint that it is effectively improve the fluidity while maintaining or improving mechanical characteristics, and suppress or prevent the fluorene derivative from bleeding out, the ratio of the fluorene derivative represented by the formula (1) relative to 100 parts by mass of the fibrous reinforcing material is more preferably 1 to 25 parts by mass, 1 to 20 parts by mass, 1.5 to 15 parts by mass, 2 to 10 parts by mass, 2.5 to 8 parts by mass, and 3 to 5 parts by mass in a stepwise manner. An excessively lower ratio of the fluorene derivative represented by the formula (1) may provide a possibility not to effectively improve the fluidity of the resin composition; and an excessively higher ratio of the fluorene derivative represented by the formula (1) may adversely affect being compatible the fluidity with mechanical characteristics, particularly the fluidity with the impact resistance, and suppress or prevent the fluorene derivative from bleeding out.

(Other Components)

The resin composition, if necessary, may or may not contain another thermoplastic resin (or second thermoplastic resin) different from a polyamide-series resin (or first thermoplastic resin).

The thermoplastic resin may include, for example, a polyolefinic resin, a styrenic resin, a (meth)acrylic resin, a vinyl acetate-series resin, a vinyl chloride-series resin, a fluororesin, a polyester-series resin, & polycarbonate-series resin (PC), a polyacetal resin (PCM), a poly(phenylene ether) resin (PPE), a polyetherketone-series resin, a phenoxy resin, a polyketone resin, a poly(phenylene sulfide) resin (PPS), a polysulfone-series resin, a cellulose derivative, a thermoplastic polyimide resin, a polyethernitrile resin, and a thermoplastic elastomer (TPE).

The polyolefinic resin may include, for example, a chain or liner olefinic resin such as a polyethylene-series resin and a polypropylene-series resin; and a cyclic olefinic resin.

The styrenic resin may include, for example, a polystyrene (PS) such as a general-purpose polystyrene (GPPS) and a syndiotactic polystyrene (SPS); and a styrenic copolymer. Examples of the styrenic copolymer may include a styrenemethyl (meth)acrylate copolymer (MS resin), a styrene-acrylonitrile copolymer (AS resin), and a rubber component-containing styrenic resin or rubber graft styrenic copolymer. The rubber component-containing styrenic resin or rubber graft styrenic copolymer may include, for example, a high impact polystyrene (HIPS), an acrylonitrile-butadiene-styrene copolymer (ABS resin), an AXS resin, and a methyl methacrylate-butadiene-styrene copolymer (MBS resin). The AXS resin may include, for example, an acrylonitrile-acrylic rubber-styrene copolymer (AAS resin), an acrylonitrile-chlorinated polyethylene-styrene copolymer (ACS resin), and an acrylonitrile-(ethylene-propylene-diene rubber)-styrene copolymer (AES resin)

Examples of the (meth)acrylic resin may include a homo- or co-polymer of a (meth)acrylic monomer such as poly(methyl methacrylate) (PMMA) and a (meth)acrylic acid-(meth)acrylate copolymer.

Examples of the vinyl acetate-series resin may include a poly(vinyl acetate) (PVAc), a poly(vinyl alcohol) (PVA), and a poly(vinyl acetal). The poly(vinyl acetal) may include, for example, a poly(vinyl formal) (PVF) and a poly(vinyl butyral) (PVB).

Examples of the vinyl chloride-series resin may include a vinyl chloride resin and a vinylidene chloride resin. The vinyl chloride resin may include, for example, a vinyl chloride homopolymer (PVC); a vinyl chloride copolymer such as a vinyl chloride-vinyl acetate copolymer. The vinylidene chloride resin may include, for example, a vinylidene chloride copolymer such as a vinylidene chloride-vinyl chloride copolymer and a vinylidene chloride-acrylonitrile copolymer.

Examples of the fluororesin may include a polytetrafluoroethylene (PTFE), a poly(chlorotrifluoroethylene) (PCTFE), a poly(vinylidene fluoride) or poly(vinylidene difluoride) (PVDF), a poly(vinyl fluoride) (PVF), a tetrafluoroethylene-hexafluoropropylene copolymer (FEP), a tetrafluoroethylene-perfluoroalkyl vinyl ether copolymer (PFA), an ethylene-tetrafluoroethylene copolymer (ETFE), and an ethylene-chlorotrifluoroethylene copolymer (ECTFE).

Examples of the polyester-series resin may include a polyalkylene arylate-series resin, a polyarylate-series resin, and a liquid crystal polyester (LCP). The polyalkylene arylate-series resin may include, for example, a poly(ethylene terephthalate) (PET), a poly(trimethylene terephthalate) (PTT), a poly(butylene terephthalate) (PBT), a poly(1,4-cyclohexyldimethylene terephthalate) (PCT), and a poly(ethylene naphthalate).

Examples of the polycarbonate-series resin (PC) may include a bisphenol polycarbonate-series resin such as a bisphenol A polycarbonate-series resin.

Examples of the polyetherketone-series resin may include a polyetherketone resin (PEK), a polyetheretherketone resin (PEEK), and a polyetherketoneetherketoneketone (PEKEKK).

Examples of the polyketone resin may include an aliphatic polyketone resin.

Examples of the polysulfone-series resin may include a polysulfone resin (PSF) and a polyethersulfone (PES).

Examples of the cellulose derivative may include a cellulose ester such as a nitrocellulose, a cellulose acetate, and a cellulose acetate propionate; and a cellulose ether such as an ethyl cellulose.

Examples of the thermoplastic polyimide resin may include a polyetherimide (PEI) and a polyamideimide.

Examples of the thermoplastic elastomer (TPE) may include a polystyrenic TPE, a polyolefinic TPE (TPO), a polydiene-series TPE, a chlorine-series TPE, a fluorine-series TPE, a polyurethane-series TPE (TPU), a polyester-series TPE (TPEE), and a polyamide-series TPE (TPA).

These second thermoplastic resins may be used alone or in combination of two or more. The ratio of the polyamide-series resin (the first thermoplastic resin) in the resin composition relative to the total thermoplastic resin (or the total of the polyamide-series resin (the first thermoplastic resin) and the second thermoplastic resin) in the resin composition may for example be about not less than 10% by mass; a preferred range of the ratio is not less than 30% by mass, not less than 50% by mass, not less than 60% by mass, not less than 70% by mass, not less than 80% by mass, not less than 90% by mass, and not less than 95% by mass in a stepwise manner; and particularly 100% by mass. An excessively lower ratio of the polyamide-series resin may provide a possibility not to improve the fluidity and/or mechanical characteristics of the rosin composition.

The resin composition, if necessary, may contain various additives such as a filler or a reinforcing agent (provided that the above fibrous reinforcing material is excluded), a colorant e.g., a dyestuff and pigment, a conductive agent, a flame retardant, a plasticizer, a lubricant, a stabilizer, a mold releasing agent, an antistatic agent, a dispersing agent, a flowability modifier, a leveling agent, an antifoamer or an antifoaming agent, a surface modifier, a low stress agent, and a carbon material (provided that the above fibrous reinforcing material is excluded), and other additives. The stabilizer may include, for example, an antioxidant, an ultraviolet absorbing agent, and a heat stabilizer. These additives may be used alone or in combination of two or more.

The resin composition can be prepared by mixing the fluorene derivative (the fluidity improving agent or the fluidity improver) and the polyamide-series resin and, if necessary, the other component such as the fibrous reinforcing material and the additive in a conventional manner such as dry blending and melt kneading or melt mixing. The resin composition may be in the form of a pellet and other forms.

(Characteristics of Resin Composition)

The resin composition has an excellent fluidity. When a resin alone, which is free from a fluorene derivative, is simply referred to as blank, and a melt flow rate (MFR) of the blank is defined as 100, a MFR of a resin composition may for example be about 110 to 500, and is preferably 130 to 450, and more preferably 160 to 400. In particular, when the resin composition contains the non-substituted amide compound as the fluorene derivative, the fluidity thereof can be further improved; and the MFR of the resin composition may be about 180 to 480, and is preferably 200 to 460, 250 to 450, 300 to 430, 330 to 410, 350 to 400, and 370 to 390 in a stepwise manner relative to 100 of the MFR of the blank. The MFR of the blank is for example 10 to 100 g/min, and preferably 20 to 60 g/min, 25 to 50 g/min, and 30 to 40 g/min in a stepwise manner.

Further, even if the fluidity thereof is improved, the resin composition does not excessively deteriorate mechanical characteristics, and can, in some cases, improve the mechanical characteristics. When a flexural strength of the blank is defined as 100, the flexural strength of the resin composition may for example be about 90 to 150, and is preferably 95 to 145, and more preferably 100 to 135. In particular, the flexural strength of the resin composition containing the non-substituted amide compound as the fluorene derivative may for example be about 110 to 140, and is preferably 120 to 130 relative to 100 of the flexural strength of the blank. The flexural strength of the blank is for example 10 to 300 MPa, and preferably 50 to 200 MPa, 80 to 10 MPa, 100 to 150 MPa, and 110 to 130 MPa in a stepwise manner.

A deflection (flexure) of the resin composition may for example be about 80 to 120, and preferably 85 to 115, more preferably 90 to 110, particularly 95 to 105, when the deflection of the blank is defined as 100. The deflection of the blank is for example 3 to 30 mm, and preferably 5 to 20 mm, 8 to 15 mm, 9 to 13 mm, and 10 to 12 mm in a stepwise manner.

A flexural modulus of the resin composition may for example be about 90 to 150, and is preferably 100 to 145, when the flexural modulus of the blank is defined as 100. In particular, the flexural modulus of the resin composition containing the non-substituted amide compound as the fluorene derivative may for example be about 110 to 150, and is preferably 120 to 140, and more preferably 125 to 135 relative to 100 of the flexural modulus of the blank. The flexural modulus of the blank is for example 1000 to 5000 MPa, and preferably 2000 to 4000 MPa, 2500 to 3500 MPa, 2700 to 3200 MPa, and 2800 to 3000 MPa in a stepwise manner.

A tensile strength (maximum tensile strength) of the resin composition may for example be about 80 to 150, and is preferably 90 to 140, and more preferably 100 to 130, when the tensile strength of the blank is defined as 100. In particular, the tensile strength of the resin composition containing the non-substituted amide compound as the fluorene derivative may for example be about 105 to 135, and is preferably 110 to 130, and more preferably 115 to 125 relative to 100 of the tensile strength of the blank. The tensile strength of the blank is for example 10 to 200 MPa, and preferably 50 to 150 MPa, 60 to 120 MPa, 70 to 100 MPa, and 30 to 90 MPa in a stepwise manner.

A tensile modulus of the resin composition may for example be about 100 to 200 when the tensile modulus of the blank is defined as 100. In particular, the tensile modulus of the resin composition containing the non-substituted amide compound as the fluorene derivative may for example be about 110 to 170, and is preferably 120 to 160, and more preferably 130 to 150 relative to 100 of the tensile modulus of the blank. The tensile modulus of the blank is for example 1000 to 5000 MPa, and preferably 2000 to 4000 MPa, 2500 to 3500 MPa, 2000 to 3200 MPa, and 2900 to 3100 MPa in a stepwise manner.

In this description and claims, the MFR, the flexural strength, the deflection, the flexural modulus, the tensile strength (maximum tensile strength), and the tensile modulus can be measured according to the methods described in Examples mentioned below.

(Molded Article (Or Molded Object))

The resin composition has excellent fluidity or mechanical characteristics, and therefore, can produce or form a molded article having an excellent mechanical characteristics with a high moldability (or productivity). The shape of the molded article is not particularly limited to a specific shape, can be selected depending on the applications, and may for example be a one-dimensional structure such as linear (a line shape) and a thread shape; a two-dimensional structure such as a film shape, a sheet shape, and a plate shape; a three-dimensional structure such as a block shape, a rod shape, and a hollow shape, e.g., a pipe shape or a tubular shape.

The molded article can be produced by conventional molding methods such as an injection molding, an injection compression molding, an extrusion molding, a transfer molding, a blow molding, a pressure molding, and a casting molding.

EXAMPLES

The following examples are intended to describe this disclosure in further detail and should by no means be interpreted as defining the scope cf the disclosure. The details of the evaluation methods and reagents used are shown below.

[Evaluation Method]

(HPLC)

The HPLC (high performance or high speed liquid chromatograph) measurement was carried out using HPLC instrument manufactured by SHIMADZU CORPORATION, "LCMS-2020", a column manufactured by SHIMADZU CORPORATION, "KINTEX XB-C18", and acetonitrile/water as a mobile phase. The volume ratio of acetonitrile/water was varied from 50/50 to 95/5 over 10 minutes, and then held at 95/5 for 5 minutes.

($^1$H-NMR)

The sample was dissolved in a heavy solvent ($CDCl_3$) containing tetramethylsilane as an internal standard substance, and the $^1$H-NMR spectrum was measured using a nuclear magnetic resonance instrument (manufactured by Bruker Corporation, "AVANCE III HD").

(Melting Point)

The melting point was measured using an instrument (manufactured by BUCHI, "Melting point M-565") under the condition of a heating rate or programming rate of 0.5° C./min from a temperature of 50° C.

(5% Mass Reduction Temperature)

The temperature, at which the mass of the sample is reduced by 5% by mass, was measured using a Thermogravimeter-Differential Thermal Analyzer (TG-DTA) (manufactured by PerkinElmer, Inc., "TGA-4000") in a nitrogen atmosphere, under the condition of a measurement temperature range of 50 to 400° C. with a heating rate of 10° C./min.

(Solvent Solubility Test)

For each sample and solvent, a sample and a solvent, shown in Table 1 below were mixed in a concentration of 3% by mass, and a mixture was shaker, by hand for about 10 minutes, and then allowed to stand overnight at a room temperature (temperature of 15 to 25° C.). The solubility of the sample was visually observed and evaluated according to the following criteria.

A: Soluble

B: Soluble, but undissolved residue was visually confirmed

C: Insoluble (Flexural Test)

The flexural strength, the deflection (flexure), and the flexural modulus were measured in accordance with JIS K 7171. The flexural modulus was calculated or measured by tangent method.

(Tensile Test)

The tensile strength (maximum tensile strength) and the tensile modulus were measured in accordance with JIS K 7161-1, and -2 under the condition of a test speed of 5 mm/min. The tensile modulus was calculated or measured by tangent method.

(MFR)

In Comparative Example 1 and Examples 1 to 6, the MFR was measured in accordance with JIS K 7210-1, B method under the conditions of the retention time of 5 minutes, the temperature of 280° C., and test load of 1.2 kg. In Comparative Example 2 and Examples 7 to 9, the MFR was measured in accordance with JIS K 7210-1. A method under the conditions of the retention time of 5 minutes, the temperature of 280° C., and test load of 2.10 kg.

(Charpy Impact Strength)

Charpy impact strength was measured in accordance with JIS K 7111.

[Reagents and Others]

(Raw Material)

N,N-diethylacrylamide: "DEAA (registered trademark)", manufactured by KJ Chemicals Corporation N,N-dimethylacrylamide: "DMAA (registered trademark)", manufactured by KJ Chemicals Corporation N-isopropylacrylamide: "KIPAM (registered trademark)", manufactured by KJ Chemicals Corporation N-acryloylmorpholine: "ACMO (registered trademark)", manufactured by KJ Chemicals Corporation Acrylamide: manufactured by FUJIFILM Wako Pure-Chemical Corporation (Others)

DMSO: dimethyl sulfoxide, manufactured by KANTO CHEMICAL CO., INC.

Toluene: manufactured by KANTO CHEMICAL CO., INC.

TBAB: tetrabutylammonium bromide, manufactured by Tokyo Chemical Industry Co., Ltd.

KOH: potassium hydroxide, manufactured by KANTO CHEMICAL CO., INC.

Isopropanol: manufactured by KANTO CHEMICAL CO., INC.

Synthesis Example 1

After charging 19.4 g (0.117 mol) of 9H-fluorene, 30 mL of DMSO, 30 mL of toluene, 0.6 g (0.0019 mol) of TBAB, and 30.5 g (0.24 mol) of N,N-diethylacrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0043 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. The obtained reaction mixture was cooled to 50° C., and was subjected to a neutralization treatment by adding 0.9 g of 10% by mass HCl aqueous solution (0.0025 mol (2.5 mmol) in terms of HCl) and 17 mL of ion-exchanged water to the reaction solution with stirring. Then, the neutralized mixture was subjected to an extraction with toluene (18.1 g), and a saturated saline (36.1 g, 3 times). The separated extract (toluene phase) was allowed to stand overnight while being cooled to 0° C., so that white crystals were precipitated. The crystals were separated by filtration, and the residue was washed with ion-exchanged water (37.3 mL), and isopropanol (10 mL) to obtain 30.2 g of the objective product represented by the following formula (1-1) (DEAA-FL; yield 61.4%).

The obtained DEAA-FL had the melting point of 87 to 39° C., and the 5% mass reduction temperature of 294° C. Further, the result of $^1$H-NMR of the obtained DEAA-FL is shown below and in FIG. 1.

[Chem. 8]

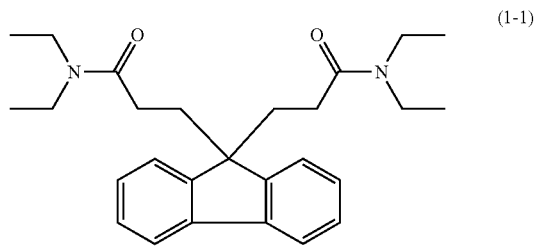

(1-1)

$^1$H-NMR (CDCl$_3$, 300 MHz): δ (ppm)=7.69-7.72 (2H, m), 7.27-7.43 (6H, m), 3.18 (4H, q), 2.79 (4H, q), 2.42-2.48 (4H, m), 1.47-1.53 (4H, m), 0.96 (6H, t), 0.76 (6H, t)

Synthesis Example 2

After charging 19.4 g (0.117 mol) of 9H-fluorene, 30 mL of DMSO, 30 mL of toluene, 0.6 g (0.0019 mol) of TBAB, and 23.8 g (0.24 mol) of N,N-dimethylacrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KQH aqueous solution (0.0043 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 mL) and isopropanol (15 mL) to obtain 30.0 g of the objective product represented by the following formula (1-2) (DMAA-FL; yield 82.4%).

The obtained DMAA-FL had the melting point of 158 to 159° C., and the 5% mass reduction temperature of 318° C. Further, the result of $^1$H-NMR of the obtained DMAA-FL is shown below and in FIG. 2.

[Chem. 9]

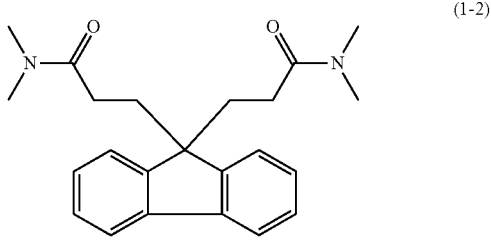

(1-2)

$^1$H-NMR (CDCl$_3$, 300 MHz): δ (ppm)=7.70-7.71 (2H, m), 7.27-7.41 (6H, m), 2.74 (6H, s), 2.51 (6H, s), 2.42-2.47 (4H, m), 1.48-1.54 (4H, m)

Synthesis Example 3

After charging 19.4 g (0.117 mol) of 9H-fluorene, 30 mL of DMSO, 30 mL of toluene, 0.6 g (0.0019 mol) of TBAB, and 27.2 g (0.24 mol) of N-isopropylacrylamide into a reactor equipped with a magnetic stirrer and a three-way cook, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCL aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 ml) and isopropanol (15 mL) to obtain 32.8 g of the objective product represented by the following formula (1-3) (NIPAM-FL; yield 71.4%).

The obtained NIPAM-FL had the melting point of 235 to 237° C., and the 5% mass reduction temperature of 257° C. Further, the result of $^1$H-NMR of the obtained NIPAM-FL is shown below and in FIG. 3.

[Chem. 10]

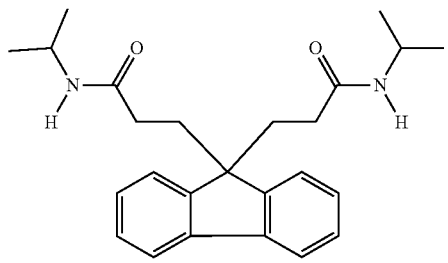

(1-3)

$^1$H-NMR (CDCl$_3$, 300 MHz): δ (ppm)=7.68-7.71 (2H, m), 7.32-7.42 (6H, m), 4.73 (2H, m), 3.84 (2H, m), 2.42 (4H, m), 1.33 (4H, m), 0.97 (12H, d)

Synthesis Example 4

After charging 19.4 g (0.117 mol) of 9H-fluorene, 30 mL of DMSO, 30 mL of toluene, 0.6 g (0.0019 mol) of TBAB, and 17.0 g (0.24 mol) of acrylamide into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.3 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 mL) and isopropanol (15 mL) to obtain 31.8 g of the objective product represented by the following formula (1-4) (AAP-FL; yield 88.4%).

The obtained AAD-FL had the melting point of 254 to 259° C., and the 5% mass reduction temperature of 320° C. Further, the result of $^1$H-NMR of the obtained AAP-FL is shown below an in FIG. 4.

[Chem. 11]

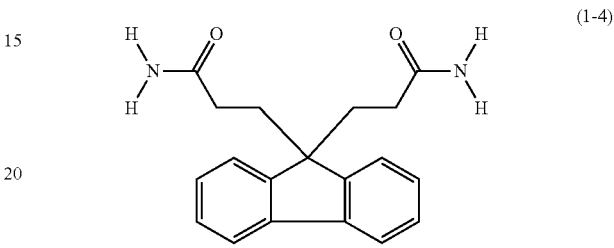

(1-4)

$^1$H-NMR (DMSO-d$_6$, 300 MHz): δ (ppm)=7.02-7.04 (2H, m), 7.47-7.49 (2H, m), 7.35-7.40 (4H, m), 6.97 (2H, s), 6.52 (2H, s), 2.24 (4H, m), 1.26 (4H, m)

Synthesis Example 5

After charging 19.4 g (0.117 mol) of 9H-fluorene, 30 mL of DMSO, 30 mL of toluene, 0.6 g (0.0019 mol) of TBAB, and 33.8 g (0.24 mol) of N-acryloylmorpholine into a reactor equipped with a magnetic stirrer and a three-way cock, and replacing the inner atmosphere of the reactor with nitrogen, the temperature was raised to 65° C. to confirm that the solid matters were completely dissolved. To the resultant solution, 0.56 g of 48% by mass KOH aqueous solution (0.0048 mol (4.8 mmol) in terms of KOH) was added, then the temperature was raised to 90° C., and the mixture was stirred while heating for 2 hours. When the disappearance of 9H-fluorene was confirmed by HPLC, the reaction was terminated. After cooling the obtained reaction mixture to 50° C., 0.9 g of 10% by mass HCl aqueous solution (0.0025 mol (2.5 mmol) in terms of HCl) and 17 mL of ion-exchanged water were added to the cooled reaction mixture, and the resulting mixture was stirred, so that white crystals gradually precipitated to form a white suspension. The suspension was subjected to a filtration, and the residue was washed with hot water (77.7 mL) and isopropanol (15 mL) to obtain the objective product represented by the following formula (1-5) (ACMO-FL).

[Chem. 12]

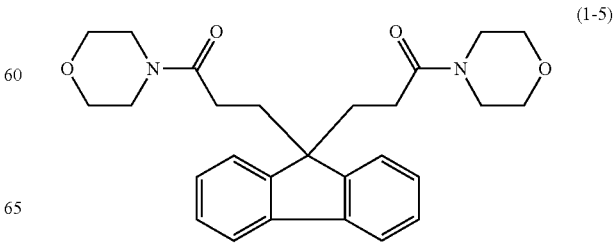

(1-5)

[Evaluation of Solubility]

The results of the solubility test of the fluorene derivatives obtained in Synthesis Examples 1 to 4 are shown in Table 1. In Table 1, IPA represents isopropanol, MEK represents methyl ethyl ketone, MIBK represents methyl isobutyl ketone, dioxane represents 1,4-dioxane, and THF represents tetrahydrofuran.

TABLE 1

|  | Synthesis Example 1 DEAA-FL | Synthesis Example 2 DMAA-FL | Synthesis Example 3 NIPAM-FL | Synthesis Example 4 AAD-FL |
|---|---|---|---|---|
| Water | C | C | C | C |
| Methanol | A | A | A | C |
| Ethanol | A | A | C | C |
| IPA | A | C | C | C |
| Acetone | A | C | C | C |
| MEK | A | C | C | C |
| MIBK | A | A | B | B |
| Ethyl acetate | A | C | C | C |
| Dioxane | A | C | C | C |
| THF | A | A | C | C |
| Toluene | A | C | C | C |
| Hexane | C | C | C | C |
| Chloroform | A | A | C | C |

[Examples 1 to 3, and Comparative Example 1]
Preparation and Evaluation of Resin Composition For each of Examples and Comparative Example, a resin composition was prepared by melt-kneading a resin and an additive with the ratio shown in Table 2 (In Comparative Example 1, without using an additive) at 280° C. using a twin-screw extruder (manufactured by Thermo Fisher Scientific K.K., "Process11 Twin Screw Extruder", L/D=40).

When a thread shaped sample obtained by extruding the resin composition was visually confirmed, the resin and the additive were compatible with each other without becoming cloudy in each of samples. Since AAD-FL in Example 3 did not have so high solubility in solvents, AAD-FL was expected to be difficult to disperse for the resin. However, AAD-FL was unexpectedly compatible with the resin.

The flexural test and the tensile test of the obtained resin composition were performed, and the MFR thereof was measured. The results are shown in Table 2. Further, the resin for preparing the resin composition is as follows.

PA66: polyamide 66, manufactured by Toray industries, Inc. "AMILAN (registered trademark) CM3001"

As apparent from Table 2, each resin composition of Examples improved the MFR without significantly reducing or decreasing a mechanical strength such as the flexural strength, the flexural modulus, the tensile strength, and the tensile modulus, in comparison with Comparative Example 1. In particular, in Example 3, the flexural strength was improved by about 26%, the flexural modulus was improved by about 29%, the tensile strength was Improved by about 13%, the tensile modulus was improved by about 33%, and the MFR was improved by about 278% (about 3.8 times) as compared with Comparative Example 1. That is, in Example 3, the mechanical strength of the resin composition is greatly improved as much as the case where a reinforcing agent (or a filler) such as a solid filler is added. In a case where such a filler is added, the fluidity of the resin composition usually tends to decrease or reduce. In contrast to these facts, unexpectedly, the MFR of the resin composition can be improved about 3.8 times, and the resin composition of Example 3 can be compatible the mechanical strength with the melt fluidity at a high level.

[Examples 4 to 6] Preparation and Evaluation of Resin Composition

For each of Examples, the PA66 as a resin and AAD-FL as an additive were kneaded at a ratio shown in Table 3 to prepare a resin composition. Kneading was performed using a twin-screw extruder (manufactured by Parker Corporation, "HK25D", L/D=41, screw diameter: 25 mm) under the conditions of a temperature of 270° C., a screw rotation speed of 150 rpm, and a discharge amount of 6 kg/hour. When a thread shaped sample obtained by extruding the resin composition was visually confirmed, the resin and the additive were compatible with each other without becoming cloudy in each of samples in Examples 4 to 6, as in Example 3.

The flexural test and the tensile test of the obtained resin composition were performed, and the MFR thereof was measured. The results together with the results of Comparative Example 1 and Example 3, are shown in Table 3.

TABLE 2

|  | Resin | Additive | | | Flexural test | | | Tensile test | | |
|---|---|---|---|---|---|---|---|---|---|---|
|  | PA66 | DEAA-FL | NIpAM-FL | AAD-FL | Flexural strength [MPa] | Deflection [mm] | Modulus [MPa] | Tensile strength [MPa] | Modulus [MPa] | MFR [g/10 min] |
|  |  | [parts by mass] | | | | | | | | |
| Comparative Example 1 | 100 | — | — | — | 118 | 11 | 2920 | 84.5 | 3040 | 35.9 |
| Example 1 | 95 | 5 | — | — | 115 | 11 | 2940 | 84.0 | 3160 | 61.9 |
| Example 2 | 95 | — | 5 | — | 124 | 11 | 3060 | 88.6 | 3160 | 50.1 |
| Example 3 | 95 | — | — | 5 | 149 | 11 | 3770 | 100 | 4190 | 136 |

TABLE 3

|  | Resin PA66 | Additive AAD-FL | Flexural test | | Tensile test | | |
| --- | --- | --- | --- | --- | --- | --- | --- |
|  | (parts by mass) | | Flexural strength [MPa] | Modulus [MPa] | Tensile strength [MPa] | Modulus [MPa | MFR [g/10 min] |
| Comparative Example 1 | 100 | — | 118 | 2920 | 84.5 | 3040 | 35.9 |
| Example 4 | 99.5 | 0.5 | 121 | 3040 | 86 | 3140 | 39 |
| Example 5 | 99 | 1 | 124 | 3070 | 87 | 3160 | 46 |
| Example 6 | 97 | 3 | 128 | 3150 | 91 | 3270 | 85 |
| Example 3 | 95 | 5 | 149 | 3770 | 100 | 4190 | 136 |

As apparent from Table 3, even in Examples 4 to 6 in which the amount of the additive was smaller than that in Example 3, the MFR could be improved while maintaining or improving the mechanical strength such as the flexural strength, the flexural modulus, the tensile strength, and the tensile modulus in comparison with Comparative Example 1. Therefore, the balance between the fluidity (MFR) and physical properties of the resin composition can be easily or effectively adjusted depending on the application.

[Examples 7 to 9, and Comparative Example 2]
Preparation and Evaluation of Resin Composition Containing Fibrous Reinforcing Material For each of Examples and Comparative Example, the PA66 as a resin, AAD-FL as an additive, and a glass fiber as a fibrous reinforcing material were kneaded with a ratio shown in Table 4 to prepare a resin composition. Kneading was performed by using a twin-screw extruder (manufactured by Toshiba Machine Co., Ltd., "TEM-26SX") and by adding a glass fiber from the side feeder under the condition of a temperature of 260° C.

The flexural test and the tensile test of the obtained resin composition were performed, and Charpy impact strength and the MFR thereof were measured. The results are shown in Table 4. In Table 4, the value in parentheses in the column of additive means the mass % of AAD-FL relative to the total amount of PA66 and AAD-FL. Further, the fibrous reinforcing material for preparing the resin composition is as follows.

GF: glass fiber, manufactured by Nippon Electric Glass Co., Ltd., "ECS03 T-275H", which is E-glass fiber chopped strand and has a filament diameter of 10.5±1.0 μm and a strand length of 3.0±1.0 mm.

the MFR could be improved without significantly reducing or decreasing (or while rather improving) mechanical characteristics due to the fibrous reinforcing material, in comparison with Comparative Example 2. While the fibrous reinforcing material can generally greatly improve the mechanical characteristics of the polyamide-series resin, the resin composition has a high viscosity to significantly deteriorate the processability (moldability or fluidity). However, in Examples 7 to 9, despite containing the fibrous reinforcing material in a higher proportion of 50% by mass in the total resin composition, the fluidity (MFR) could be greatly improved by using a small amount of the additive. Such results or facts can be confirmed from the comparison of the MFRs of Examples 7 and 8, with the corresponding MFRs of Examples 6 and 3 (Examples containing the same amount of AAD-FL relative to PA66, and no containing GF). That is, the MFRs of Examples 7 and 8 were improved about 2.4 times and 4.0 times, respectively, as compared with Comparative Example 2 (no additive), whereas the MFRs of Examples 6 and 3 were improved about 2.4 times and 3.8 times, respectively, as compared with Comparative Example 1 (no additive); and thus even if the resin compositions in Examples 7 and 8 contain a higher proportion of GF, the MFR thereof could be improved to the same level as or higher than that in Examples 6 and 3.

Further, in Examples 7 to 9, the MFR could be notably improved without significantly reducing the impact strength; and the resin composition could be compatible high impact resistance with high fluidity in a well-balanced manner.

INDUSTRIAL APPLICABILITY

The resin composition of the present disclosure can effectively improve moldability, since the fluidity (or mold-

TABLE 4

|  | PA66 | AAD-FL [parts by mass] | Fibrous reinforcing material GF | Flexural test | | Tensile strength [MPa] | Charpy impact strength [kJ/m²] | MFR [g/10 min] |
| --- | --- | --- | --- | --- | --- | --- | --- | --- |
|  | | | | Flexural strength [MPa] | Modulus [GPa] | | | |
| Comprative Example 1 | 50 | — (0%) | 50 | 358 | 14.8 | 225 | 15.1 | 9.7 |
| Example 7 | 48.5 | 1.5 (3%) | 50 | 357 | 14.7 | 230 | 15.2 | 23.5 |
| Example 8 | 47.5 | 2.5 (5%) | 50 | 357 | 15.2 | 229 | 13.5 | 39.0 |
| Example 9 | 45 | 5 (10%) | 50 | 350 | 15.3 | 230 | 12.6 | 91.1 |

As apparent from Table 4, in the resin composition of Examples 7 to 9 containing a fibrous reinforcing material, ability) such as the melt fluidity of the resin composition can be significantly improved without excessively reducing or while improving the mechanical strength of the polyamide-series resin. Therefore, with utilizing the fact that the polyamide-series resin has excellent properties such as wear resistance, lubricity, heat resistance, and chemical resistance; the resin composition of the present disclosure can be used in a wide range of applications such as a fiber, a film, a daily necessity, an automobile-related parts, an electrical/electronic-related parts, a machine-related parts, a construction-related parts, and a sports/leisure-related parts. Specifically, the resin composition of the present, disclosure can be used for a rope, a tire cord, a fishing net, a filter cloth, a clothing core material, a packaging film, a radiator tank, a manifold, a piping tube and pipe, a hose, an air cleaner, a clutch parts, a connector (including an electric circuit connector), a switch, a gear, a pulley, a cam, a bush, a roller, a bearing, a housing, a casing, a wire coating, a door roller, a rail parts, a caster, a shoes, a shuttlecock, and a reel.

The invention claimed is:

1. A resin composition comprising a compound represented by the following formula (1), and a polyamide-series resin:

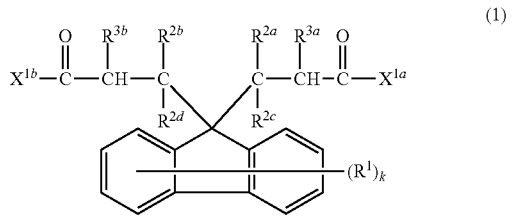
(1)

wherein $R^1$ represents a hydrocarbon group bonded to any substitutable position on either benzene ring of the fluorene ring, k denotes an integer of 0 to 8, $R^{2a}$, $R^{2b}$, $R^{2c}$, and $R^{2d}$ independently represent a hydrogen atom or a hydrocarbon group, $R^{3a}$ and $R^{3b}$ independently represent a hydrogen atom or a hydrocarbon group, and $X^{1a}$ and $X^{1b}$ independently represent a group defined in the following formula (X1):

(X1)

wherein $R^4$ and $R^5$ independently represent a hydrogen atom or a hydrocarbon group; or $R^4$ and $R^5$ bond together to form a heterocyclic ring containing the nitrogen atom adjacent to $R^4$ and $R^5$.

2. The resin composition according to claim 1, wherein, in the formula (1), $R^4$ and $R^5$ each represent a hydrogen atom.

3. The resin composition according to claim 1, wherein the polyamide-series resin is an aliphatic polyamide resin.

4. The resin composition according to claim 1, wherein the mass ratio of the compound represented by the formula (1) relative to the polyamide-series resin is 1/99 to 10/90 in terms of the former/the latter.

5. The resin composition according to claim 1, which further comprises a fibrous reinforcing material.

6. The resin composition according to claim 5, wherein the fibrous reinforcing material is an inorganic fiber.

7. The resin composition according to claim 5, wherein the ratio of the compound represented by the formula (1) is 0.5 to 100 parts by mass relative to 100 parts by mass of the fibrous reinforcing material.

8. A method for improving the fluidity of a polyamide-series resin, which comprises adding a compound represented by the formula (1) according to claim 1 to the polyamide-series resin.

9. A method of improving the fluidity of a polyamide-series resin, comprising:

combining a compound represented by the following formula (1),

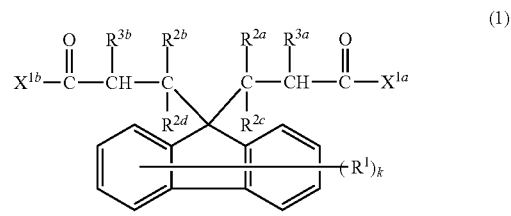
(1)

wherein $R^1$ represents a hydrocarbon group bonded to any substitutable position on either benzene ring of the fluorene ring, k denotes an integer of 0 to 8, $R^{2a}$, $R^{2b}$, $R^{2c}$, and $R^{2d}$ independently represent a hydrogen atom or a hydrocarbon group, $R^{3a}$ and $R^{3b}$ independently represent a hydrogen atom or a hydrocarbon group, and $X^{1a}$ and $X^{1b}$ independently represent a group defined in the following formula (X1):

(X1)

wherein $R^4$ and $R^5$ independently represent a hydrogen atom or a hydrocarbon group; or $R^4$ and $R^5$ bond together to form a heterocyclic ring containing the nitrogen atom adjacent to $R^4$ and $R^5$, with a polyamide-series resin, to obtain a resin composition comprising the polyamide-series resin having improved fluidity.

* * * * *